(12) United States Patent
Lee et al.

(10) Patent No.: US 11,945,878 B2
(45) Date of Patent: Apr. 2, 2024

(54) SWITCH MOLECULE AND SWITCHABLE CHIMERIC ANTIGEN RECEPTOR

(71) Applicant: ABCLON INC., Seoul (KR)

(72) Inventors: Jong Seo Lee, Gyeonggi-do (KR); Carl Erik Mathias Uhlen, Stockholm (SE)

(73) Assignee: ABCLON INC., Seoul (KR)

( * ) Notice: Subject to any disclaimer, the term of this patent is extended or adjusted under 35 U.S.C. 154(b) by 79 days.

(21) Appl. No.: 17/048,739

(22) PCT Filed: Apr. 18, 2019

(86) PCT No.: PCT/KR2019/004720
§ 371 (c)(1),
(2) Date: Oct. 19, 2020

(87) PCT Pub. No.: WO2019/203600
PCT Pub. Date: Oct. 24, 2019

(65) Prior Publication Data
US 2021/0130490 A1    May 6, 2021

(30) Foreign Application Priority Data

Apr. 18, 2018 (KR) .................. 10-2018-0045228

(51) Int. Cl.
C07K 16/32 (2006.01)
C07K 16/28 (2006.01)

(52) U.S. Cl.
CPC .............. C07K 16/32 (2013.01); C07K 16/28 (2013.01); C07K 16/2803 (2013.01); C07K 2317/622 (2013.01); C07K 2318/20 (2013.01); C07K 2319/21 (2013.01)

(58) Field of Classification Search
None
See application file for complete search history.

(56) References Cited

U.S. PATENT DOCUMENTS

2018/0100026 A1    4/2018   Kim et al.

FOREIGN PATENT DOCUMENTS

| | | | |
|---|---|---|---|
| CN | 106574272 A | 4/2017 | |
| CN | 107074975 A | 8/2017 | |
| JP | 2014-507118 A | 3/2014 | |
| JP | 2016-533174 A | 10/2016 | |
| JP | 2016-534995 A | 11/2016 | |
| KR | 2016-0062760 A | 6/2016 | |
| WO | WO-2014096163 A1 * | 6/2014 | ............... A61P 1/02 |
| WO | WO-2016-154621 A1 | 9/2016 | |
| WO | WO-2016-168773 A2 | 10/2016 | |
| WO | WO-2017/172981 A2 | 10/2017 | |

OTHER PUBLICATIONS

Cowton et al (npj Vaccines, 6(7):1-10, 2021).*
Nygren, Per-Ake (FEBS, 275:2668-2676, 2008).*
Arcangeli, S. et al. (2016) "Switchable chimeric antigen receptor T cells: a novel universal chimeric antigen receptor platfom for a safe control of T-cell activation.", *Translational Cancer Research*, 5(S2):SI74-SI77.
Eklund, M. et al. (2002) "Anti-idiotypic protein domains selected from protein A-based affibody libraries.", *Proteins: Structure, Function, and Bioinformatics*. 48(3):454-462.
Zhang, E. et al. (2017) "A new insight in chimeric antigen receptor-engineered T cells for cancer immunotherapy.", *Journal of Hematology & Oncology*, 10(1):1-11.
International Search Report from corresponding PCT Application No. PCT/KR2019/004720, dated Aug. 12, 2019, with English translation.
ESR of EP Patent Application No. 19787870.5 dated Jul. 14, 2021.
Office Action of JP Patent Application No. 2020-557989 dated Oct. 5, 2021.
Ma, J. S. Y., et al.; "Versatile strategy for controlling the specificity and activity of engineered T cells", PNAS, E450-458, Jan. 12, 2016.
Cartellieri, M., et al.; "Switching CAR T cells on and off: a novel modular platform for retargeting of T cells to AML blasts" Blood Cancer Journal (2016) 6, e458; doi:10.1038/bcj.2016.61, pp. 1-8.
Klesmith, J. R . . . et al.; "Retargeting CD19 Chimeric Antigen Receptor T Cells via Engineered CD19-Fusion Proteins", Mol. Pharmaceutics 2019. 16. 3544-3558.
Office Action from corresponding Chinese Patent Application No. 201980026597.8, dated Mar. 23, 2023.
Lendel, C., et al.; "Structural Basis for Molecular Recognition in an Affibody: Affibody Complex", J. Mol. Biol. (2006) 359, 1293-1304.

(Continued)

*Primary Examiner* — Brad Duffy

(57) ABSTRACT

The present invention relates to a switch molecule for activating a chimeric antigen receptor effector cell, to a polypeptide or fusion protein binding thereto, and to a chimeric antigen receptor. (i) When a switch molecule of the present invention is used, in order to improve safety of a CAR-T cell, if severe toxicity appears, a switch molecule lacking a targeting moiety can be injected to adjust activation of the CAR-T cell. (ii) When an antigen is mutated, or in order to cure various carcinomas, instead of an existing switch molecule, a switch molecule targeting a new antigen generated due to the mutation or a switch molecule targeting a different tumor associated antigen (TAA) can be injected into a patient to cure cancer more effectively.

2 Claims, 13 Drawing Sheets

Specification includes a Sequence Listing.

(56) References Cited

OTHER PUBLICATIONS

Office Action from corresponding Japanese Patent Application No. 2020-557989, dated Jan. 23, 2024.
Graille M. et al., "Crystal structure of a *Staphylococcus aureus* protein A domain complexed with the Fab fragment of a human IgM antibody: Structural basis for recognition of B-cell receptors and superantigen activity", PNAS, 2000, vol. 97, No. 10, pp. 5399-5404.
Jansson B. et al., "All individual domains of staphylococcal protein A show Fab binding" FEMS Immunology and Medical Microbiology, 1998, vol. 20, pp. 69-78.

\* cited by examiner

| scCD19-(S4G)3-Zb1 | 81_scFv | (S₄G)₃ | Zb1 | His |
| scCD19-(G4S)3-Zb1 | 81_scFv | (G₄S)₃ | Zb1 | His |
| scCD19-(S4G)3-Zb2 | 81_scFv | (S₄G)₃ | Zb2 | His |
| scCD19-(G4S)3-Zb2 | 81_scFv | (G₄S)₃ | Zb2 | His |

FIG. 6

SEQUENCE LISTING

```
<160> NUMBER OF SEQ ID NOS: 29

<210> SEQ ID NO 1
<211> LENGTH: 198
<212> TYPE: DNA
<213> ORGANISM: Artificial Sequence
<220> FEATURE:
<223> OTHER INFORMATION: Nucleic acid sequence for encoding Zb1-His tag

<400> SEQUENCE: 1
gtcgataaca aattcaacaa agagctgggc tgggctacct gggagatttt taatcttccg      60
aatttaaacg gtgttcaagt gaaagctttt atcgatagcc tgcgcgacga tcctagccag     120
agcgcaaatt tgctggccga agcaaaaaaa ctgaatgatg cgcaggcgcc aaagctcgag     180
caccaccacc accaccac                                                    198

<210> SEQ ID NO 2
<211> LENGTH: 66
<212> TYPE: PRT
<213> ORGANISM: Artificial Sequence
<220> FEATURE:
<223> OTHER INFORMATION: Amino acid sequence of Zb1-His tag

<400> SEQUENCE: 2

Val Asp Asn Lys Phe Asn Lys Glu Leu Gly Trp Ala Thr Trp Glu Ile
1               5                   10                  15

Phe Asn Leu Pro Asn Leu Asn Gly Val Gln Val Lys Ala Phe Ile Asp
            20                  25                  30

Ser Leu Arg Asp Asp Pro Ser Gln Ser Ala Asn Leu Leu Ala Glu Ala
        35                  40                  45
```

Lys Lys Leu Asn Asp Ala Gln Ala Pro Lys Leu Glu His His His His
    50                  55                  60

His His
65

<210> SEQ ID NO 3
<211> LENGTH: 198
<212> TYPE: DNA
<213> ORGANISM: Artificial Sequence
<220> FEATURE:
<223> OTHER INFORMATION: Nucleic acid sequence for encoding Zb2-His tag

<400> SEQUENCE: 3
gtcgataaca aattcaacaa agagcgcgta attgcaatcg gtgaaattat gcgtctgcca      60
aacctgaata gcctgcaggt tgtggccttt ataaactctc tgcgcgatga cccgagtcag     120
tcagcaaacc tgcttgcgga agcgaaaaag ctgaatgatg cccaagctcc taaactcgag     180
caccaccacc accaccac                                                   198

<210> SEQ ID NO 4
<211> LENGTH: 66
<212> TYPE: PRT
<213> ORGANISM: Artificial Sequence
<220> FEATURE:
<223> OTHER INFORMATION: Amino acid sequence of Zb2-His tag

<400> SEQUENCE: 4

Val Asp Asn Lys Phe Asn Lys Glu Arg Val Ile Ala Ile Gly Glu Ile
1               5                   10                  15

Met Arg Leu Pro Asn Leu Asn Ser Leu Gln Val Val Ala Phe Ile Asn
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys Leu Glu His His His His
    50                  55                  60

His His
65

<210> SEQ ID NO 5
<211> LENGTH: 885
<212> TYPE: DNA
<213> ORGANISM: Artificial Sequence
<220> FEATURE:
<223> OTHER INFORMATION: Nucleic acid sequence for encoding Zb1-Fc

<400> SEQUENCE: 5
gtcgataaca aattcaacaa agagctgggc tgggctacct gggagatttt taatcttccg      60
aatttaaacg gtgttcaagt gaaagctttt atcgatagcc tgcgcgacga tcctagccag     120
agcgcaaatt tgctggccga agcaaaaaaa ctgaatgatg cgcaggcgcc aaagggccag     180
gccggccagg agcccaaatc tagcgacaaa actcacacaa gcccaccgtg cccagcacct     240
gaactcctgg ggggaccgtc agtcttcctc ttccccccaa acccaaggga caccctcatg     300
atctcccgga cccctgaggt cacatgcgtg gtggtggacg tgagccacga agaccctgag     360
gtcaagttca actggtacgt ggacggcgtg gaggtgcata atgccaagac aaagccgcgg     420
gaggagcagt acaacagcac gtaccgtgtg gtcagcgtcc tcaccgtcct gcaccaggac     480
tggctgaatg gcaaggagta caagtgcaag gtctccaaca aagccctccc agcccccatc     540
gagaaaacca tctccaaagc caaagggcag ccccgagaac cacaggtgta caccctgccc     600

```
ccatcccggg atgagctgac caagaaccag gtcagcctga cctgcctggt caaaggcttc    660
tatcccagcg acatcgccgt ggagtgggag agcaatgggc agccggagaa caactacaag    720
accacgcctc ccgtgctgga ctccgacggc tccttcttcc tctacagcaa gctcaccgtg    780
gacaagagca ggtggcagca ggggaacgtc ttctcatgct ccgtgatgca tgaggctctg    840
cacaaccact acacgcagaa gagcctctcc ctgtccccgg gtaaa                    885
```

<210> SEQ ID NO 6
<211> LENGTH: 295
<212> TYPE: PRT
<213> ORGANISM: Artificial Sequence
<220> FEATURE:
<223> OTHER INFORMATION: Amino acid sequence of Zb1-Fc

<400> SEQUENCE: 6

```
Val Asp Asn Lys Phe Asn Lys Glu Leu Gly Trp Ala Thr Trp Glu Ile
1               5                   10                  15

Phe Asn Leu Pro Asn Leu Asn Gly Val Gln Val Lys Ala Phe Ile Asp
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys Gly Gln Ala Gly Gln Glu
    50                  55                  60

Pro Lys Ser Ser Asp Lys Thr His Thr Ser Pro Cys Pro Ala Pro
65                  70                  75                  80

Glu Leu Leu Gly Gly Pro Ser Val Phe Leu Phe Pro Pro Lys Pro Lys
                85                  90                  95

Asp Thr Leu Met Ile Ser Arg Thr Pro Glu Val Thr Cys Val Val Val
            100                 105                 110

Asp Val Ser His Glu Asp Pro Glu Val Lys Phe Asn Trp Tyr Val Asp
        115                 120                 125

Gly Val Glu Val His Asn Ala Lys Thr Lys Pro Arg Glu Glu Gln Tyr
    130                 135                 140

Asn Ser Thr Tyr Arg Val Val Ser Val Leu Thr Val Leu His Gln Asp
145                 150                 155                 160

Trp Leu Asn Gly Lys Glu Tyr Lys Cys Lys Val Ser Asn Lys Ala Leu
                165                 170                 175

Pro Ala Pro Ile Glu Lys Thr Ile Ser Lys Ala Lys Gly Gln Pro Arg
            180                 185                 190

Glu Pro Gln Val Tyr Thr Leu Pro Pro Ser Arg Asp Glu Leu Thr Lys
        195                 200                 205

Asn Gln Val Ser Leu Thr Cys Leu Val Lys Gly Phe Tyr Pro Ser Asp
    210                 215                 220

Ile Ala Val Glu Trp Glu Ser Asn Gly Gln Pro Glu Asn Asn Tyr Lys
225                 230                 235                 240

Thr Thr Pro Pro Val Leu Asp Ser Asp Gly Ser Phe Phe Leu Tyr Ser
                245                 250                 255

Lys Leu Thr Val Asp Lys Ser Arg Trp Gln Gln Gly Asn Val Phe Ser
            260                 265                 270

Cys Ser Val Met His Glu Ala Leu His Asn His Tyr Thr Gln Lys Ser
        275                 280                 285

Leu Ser Leu Ser Pro Gly Lys
    290                 295
```

<210> SEQ ID NO 7
<211> LENGTH: 885
<212> TYPE: DNA
<213> ORGANISM: Artificial Sequence
<220> FEATURE:
<223> OTHER INFORMATION: Nucleic acid sequence for encoding Zb2-Fc

<400> SEQUENCE: 7

```
gtcgataaca aattcaacaa agagcgcgta attgcaatcg gtgaaattat gcgtctgcca    60
aacctgaata gcctgcaggt tgtggccttt ataaactctc tgcgcgatga cccgagtcag   120
tcagcaaacc tgcttgcgga agcgaaaaag ctgaatgatg cccaagctcc taaaggccag   180
gccggccagg agcccaaatc tagcgacaaa actcacacaa gccccaccgtg cccagcacct   240
gaactcctgg ggggaccgtc agtcttcctc ttccccccaa acccaagga caccctcatg   300
atctcccgga cccctgaggt cacatgcgtg gtggtggacg tgagccacga agaccctgag   360
gtcaagttca actggtacgt ggacggcgtg gaggtgcata atgccaagac aaagccgcgg   420
gaggagcagt acaacagcac gtaccgtgtg gtcagcgtcc tcaccgtcct gcaccaggac   480
tggctgaatg gcaaggagta caagtgcaag gtctccaaca agcccctccc agccccatc   540
gagaaaacca tctccaaagc caagggcag ccccgagaac acaggtgta cacccctgccc   600
ccatcccggg atgagctgac caagaaccag gtcagcctga cctgcctggt caaaggcttc   660
tatcccagcg acatcgccgt ggagtgggag agcaatgggc agccggagaa caactacaag   720
accacgcctc ccgtgctgga ctccgacggc tccttcttcc tctacagcaa gctcaccgtg   780
gacaagagca ggtggcagca ggggaacgtc ttctcatgct ccgtgatgca tgaggctctg   840
cacaaccact acacgcagaa gagcctctcc ctgtccccgg gtaaa              885
```

<210> SEQ ID NO 8
<211> LENGTH: 295
<212> TYPE: PRT
<213> ORGANISM: Artificial Sequence
<220> FEATURE:
<223> OTHER INFORMATION: Amino acid sequence of Zb2-Fc

<400> SEQUENCE: 8

```
Val Asp Asn Lys Phe Asn Lys Glu Arg Val Ile Ala Ile Gly Glu Ile
 1               5                   10                  15

Met Arg Leu Pro Asn Leu Asn Ser Leu Gln Val Val Ala Phe Ile Asn
            20                  25                  30

Ser Leu Arg Asp Asp Pro Ser Gln Ser Ala Asn Leu Leu Ala Glu Ala
        35                  40                  45

Lys Lys Leu Asn Asp Ala Gln Ala Pro Lys Gly Gln Ala Gly Gln Glu
    50                  55                  60

Pro Lys Ser Ser Asp Lys Thr His Thr Ser Pro Pro Cys Pro Ala Pro
65                  70                  75                  80

Glu Leu Leu Gly Gly Pro Ser Val Phe Leu Phe Pro Pro Lys Pro Lys
                85                  90                  95

Asp Thr Leu Met Ile Ser Arg Thr Pro Glu Val Thr Cys Val Val Val
            100                 105                 110

Asp Val Ser His Glu Asp Pro Glu Val Lys Phe Asn Trp Tyr Val Asp
        115                 120                 125

Gly Val Glu Val His Asn Ala Lys Thr Lys Pro Arg Glu Glu Gln Tyr
    130                 135                 140

Asn Ser Thr Tyr Arg Val Val Ser Val Leu Thr Val Leu His Gln Asp
145                 150                 155                 160
```

```
Trp Leu Asn Gly Lys Glu Tyr Lys Cys Lys Val Ser Asn Lys Ala Leu
            165                 170                 175
Pro Ala Pro Ile Glu Lys Thr Ile Ser Lys Ala Lys Gly Gln Pro Arg
        180                 185                 190
Glu Pro Gln Val Tyr Thr Leu Pro Pro Ser Arg Asp Glu Leu Thr Lys
    195                 200                 205
Asn Gln Val Ser Leu Thr Cys Leu Val Lys Gly Phe Tyr Pro Ser Asp
210                 215                 220
Ile Ala Val Glu Trp Glu Ser Asn Gly Gln Pro Glu Asn Asn Tyr Lys
225                 230                 235                 240
Thr Thr Pro Pro Val Leu Asp Ser Asp Gly Ser Phe Phe Leu Tyr Ser
                245                 250                 255
Lys Leu Thr Val Asp Lys Ser Arg Trp Gln Gln Gly Asn Val Phe Ser
            260                 265                 270
Cys Ser Val Met His Glu Ala Leu His Asn His Tyr Thr Gln Lys Ser
        275                 280                 285
Leu Ser Leu Ser Pro Gly Lys
    290                 295
```

```
<210> SEQ ID NO 9
<211> LENGTH: 393
<212> TYPE: DNA
<213> ORGANISM: Artificial Sequence
<220> FEATURE:
<223> OTHER INFORMATION: Nucleic acid sequence for encoding
      zHER2-(S4G)3-Zb1

<400> SEQUENCE: 9
gttgacaaca agtttaacaa ggaaatgcgt aacgcgtact gggaaattgc cctgctgcca      60
aatctgaata accagcagaa acgtgctttc atccgcagcc tgtatgacga tcctagccag     120
agcgccaatc tgcttgctga ggcaaaaaaa ttgaatgatg cgcaagcacc gaaatcatca     180
agcagtggaa gttcttcatc cggctcatca tcttcaggtg tcgataacaa attcaacaaa     240
gagctgggct gggctaccta ggagattttt aatcttccga atttaaacgg tgttcaagtg     300
aaagctttta tcgatagcct gcgcgacgat cctagccaga gcgcaaattt gctggccgaa     360
gcaaaaaaac tgaatgatgc gcaggcgcca aag                                   393
```

```
<210> SEQ ID NO 10
<211> LENGTH: 131
<212> TYPE: PRT
<213> ORGANISM: Artificial Sequence
<220> FEATURE:
<223> OTHER INFORMATION: Amino acid sequence of zHER2-(S4G)3-Zb1

<400> SEQUENCE: 10

Val Asp Asn Lys Phe Asn Lys Glu Met Arg Asn Ala Tyr Trp Glu Ile
1               5                  10                  15
Ala Leu Leu Pro Asn Leu Asn Asn Gln Gln Lys Arg Ala Phe Ile Arg
            20                  25                  30
Ser Leu Tyr Asp Asp Pro Ser Gln Ser Ala Asn Leu Leu Ala Glu Ala
        35                  40                  45
Lys Lys Leu Asn Asp Ala Gln Ala Pro Lys Ser Ser Ser Gly Ser
    50                  55                  60
Ser Ser Ser Gly Ser Ser Ser Gly Val Asp Asn Lys Phe Asn Lys
65                  70                  75                  80
Glu Leu Gly Trp Ala Thr Trp Glu Ile Phe Asn Leu Pro Asn Leu Asn
                85                  90                  95
```

Gly Val Gln Val Lys Ala Phe Ile Asp Ser Leu Arg Asp Asp Pro Ser
                100                 105                 110

Gln Ser Ala Asn Leu Leu Ala Glu Ala Lys Lys Leu Asn Asp Ala Gln
            115                 120                 125

Ala Pro Lys
    130

<210> SEQ ID NO 11
<211> LENGTH: 948
<212> TYPE: DNA
<213> ORGANISM: Artificial Sequence
<220> FEATURE:
<223> OTHER INFORMATION: Nucleic acid sequence for encoding
      scHER2-(S4G)3-Zb1

<400> SEQUENCE: 11

```
gacattcaga tgacgcagtc accatcgtcg ttgtcagcgt cggtaggtga tcgcgtcacg      60
attacctgtc gtgcatccca agatgtgaac actgcagtag cgtggtacca gcagaaaccg    120
gggaaagctc cgaaacttct gatttactcg gcgagtttcc tgtatagtgg cgttccaagt    180
cgctttagcg gttcccgttc tggcacggat ttcacactga ccatctcaag cttgcagccg    240
gaagattttg ccacctatta ctgccaacag cactatacca ctcctccgac ctttggccaa    300
ggcaccaaag tggagatcaa acgcggcgga ggtggtagtg gtggcggtgg gtctggcggc    360
ggtgggagcg aagtgcagct ggtcgaatcg ggtggcggat tagtgcagcc tggaggctcc    420
ttacgcctga gctgtgcagc gagcggcttc aacatcaagg acacctacat acattgggtt    480
cgccaagctc cgggcaaagg tctggagtgg gttgctcgta tctatcccac taatgggtat    540
acacgctatg ccgatagcgt gaaaggccgg tttaccatta cgccgatac  gagcaagaat    600
acggcgtatc tgcagatgaa ctctctgcgt gccgaagata cagcggtcta ctactgctct    660
cgttggggtg gtgacgggtt ttatgcaatg gactattggg gccaaggaac cctcgtgacg    720
gtttcctcat catcaagcag tggaagttct tcatccggct catcatcttc aggtgtcgat    780
aacaaattca caaagagct  gggctgggct acctgggaga ttttaatct  tccgaattta    840
aacggtgttc aagtgaaagc ttttatcgat agcctgcgcg acgatcctag ccagagcgca    900
aatttgctgg ccgaagcaaa aaaactgaat gatgcgcagg cgccaaag               948
```

<210> SEQ ID NO 12
<211> LENGTH: 316
<212> TYPE: PRT
<213> ORGANISM: Artificial Sequence
<220> FEATURE:
<223> OTHER INFORMATION: Amino acid sequence of scHER2-(S4G)3-Zb1

<400> SEQUENCE: 12

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro

|  | 85 |  |  | 90 |  |  | 95 |  |
|---|---|---|---|---|---|---|---|---|

Thr Phe Gly Gln Gly Thr Lys Val Glu Ile Lys Arg Gly Gly Gly
                      100                    105                    110

Ser Gly Gly Gly Ser Gly Gly Gly Ser Glu Val Gln Leu Val
    115                    120                    125

Glu Ser Gly Gly Gly Leu Val Gln Pro Gly Gly Ser Leu Arg Leu Ser
    130                    135                    140

Cys Ala Ala Ser Gly Phe Asn Ile Lys Asp Thr Tyr Ile His Trp Val
145                    150                    155                    160

Arg Gln Ala Pro Gly Lys Gly Leu Glu Trp Val Ala Arg Ile Tyr Pro
                    165                    170                    175

Thr Asn Gly Tyr Thr Arg Tyr Ala Asp Ser Val Lys Gly Arg Phe Thr
                180                    185                    190

Ile Ser Ala Asp Thr Ser Lys Asn Thr Ala Tyr Leu Gln Met Asn Ser
    195                    200                    205

Leu Arg Ala Glu Asp Thr Ala Val Tyr Tyr Cys Ser Arg Trp Gly Gly
    210                    215                    220

Asp Gly Phe Tyr Ala Met Asp Tyr Trp Gly Gln Gly Thr Leu Val Thr
225                    230                    235                    240

Val Ser Ser Ser Ser Ser Gly Ser Ser Ser Gly Ser Ser Ser
                    245                    250                    255

Ser Gly Val Asp Asn Lys Phe Asn Lys Glu Leu Gly Trp Ala Thr Trp
    260                    265                    270

Glu Ile Phe Asn Leu Pro Asn Leu Asn Gly Val Gln Val Lys Ala Phe
    275                    280                    285

Ile Asp Ser Leu Arg Asp Asp Pro Ser Gln Ser Ala Asn Leu Leu Ala
    290                    295                    300

Glu Ala Lys Lys Leu Asn Asp Ala Gln Ala Pro Lys
305                    310                    315

<210> SEQ ID NO 13
<211> LENGTH: 1569
<212> TYPE: DNA
<213> ORGANISM: Artificial Sequence
<220> FEATURE:
<223> OTHER INFORMATION: Nucleic acid sequence for encoding igHER2 heavy
     chain-(S4G)3-Zb1

<400> SEQUENCE: 13

```
gaggtgcagc tggtggaatc tggcggagga ctggtgcagc ctggcggctc tctgagactg      60
tcttgtgccg cctccggctt caacatcaag gacacctaca tccactgggt ccgacaggcc     120
cctggcaagg gactggaatg ggtggcccgg atctacccca ccaacggcta caccagatac     180
gccgactccg tgaagggccg gttcaccatc tccgccgaca cctccaagaa caccgcctac     240
ctgcagatga actccctgag agccgaggac accgccgtgt actactgctc cagatgggga     300
ggcgacggct tctacgctat ggactattgg ggccagggca ccctggtcac cgtgtcctct     360
gcttctacca agggcccctc cgtgttccct ctggccccct ccagcaagtc cacctctggc     420
ggaaccgctg ctctgggctg cctggtcaag gactacttcc ccgagcctgt gaccgtgtcc     480
tggaactctg gcgctctgac ctccggcgtg cacaccttc cagccgtgct gcagtcctcc     540
ggcctgtact ctctgtcctc cgtcgtgacc gtgccttcca gctctctggg cacccagacc     600
tacatctgca acgtgaacca caagccctcc aacaccaagg tggacaagaa ggtgaacccc     660
aagtcctgcg acaagaccca cacctgtccc ccttgtcctg cccctgaact gctgggcgga     720
```

```
ccttccgtgt tcctgttccc cccaaagccc aaggacaccc tgatgatctc ccggaccccc    780
gaagtgacct gcgtggtggt ggatgtgtcc cacgaggacc ctgaagtgaa gttcaattgg    840
tacgtggacg gcgtggaagt gcacaacgcc aagaccaagc ccagagagga acagtacaac    900
tccacctacc gggtggtgtc cgtgctgacc gtgctgcacc aggactggct gaacggcaaa    960
gagtacaagt gcaaggtgtc caacaaggcc ctgcctgccc ccatcgaaaa gaccatctcc   1020
aaggccaagg gccagccccg cgagcctcag gtgtacacac tgccccccag ccgggaagag   1080
atgaccaaga accaggtgtc cctgacctgt ctggtcaagg gcttctaccc ctccgacatt   1140
gccgtggaat gggagtccaa cggccagccc gagaacaact acaagaccac ccccctgtg    1200 ctggactccg acggctcatt cttcctgtac tccaagctga ccgtggacaa gtcccggtgg   1260
cagcagggca acgtgttctc ctgctctgtg atgcacgagg ccctgcacaa ccactacacc   1320
cagaagtccc tgtccctgag ccccggcaag tcatcaagca gtggaagttc ttcatccggc   1380
tcatcatctt caggtgtcga taacaaattc aacaaagagc tgggctgggc tacctgggag   1440
atttttaatc ttccgaattt aaacggtgtt caagtgaaag cttttatcga tagcctgcgc   1500
gacgatccta gccagagcgc aaatttgctg gccgaagcaa aaaaactgaa tgatgcgcag   1560
gcgccaaag                                                           1569
```

<210> SEQ ID NO 14
<211> LENGTH: 523
<212> TYPE: PRT
<213> ORGANISM: Artificial Sequence
<220> FEATURE:
<223> OTHER INFORMATION: Amino acid sequence of igHER2 heavy
      chain-(S4G)3-Zb1

<400> SEQUENCE: 14

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Val Val Thr Val Pro
            180                 185                 190

Ser Ser Ser Leu Gly Thr Gln Thr Tyr Ile Cys Asn Val Asn His Lys
        195                 200                 205
```

-continued

```
Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys Ser Ser Ser Gly Ser Ser Ser Gly Ser Ser Ser Ser
    450                 455                 460

Gly Val Asp Asn Lys Phe Asn Lys Glu Leu Gly Trp Ala Thr Trp Glu
465                 470                 475                 480

Ile Phe Asn Leu Pro Asn Leu Asn Gly Val Gln Val Lys Ala Phe Ile
                485                 490                 495

Asp Ser Leu Arg Asp Asp Pro Ser Gln Ser Ala Asn Leu Leu Ala Glu
            500                 505                 510

Ala Lys Lys Leu Asn Asp Ala Gln Ala Pro Lys
        515                 520
```

<210> SEQ ID NO 15
<211> LENGTH: 642
<212> TYPE: DNA
<213> ORGANISM: Artificial Sequence
<220> FEATURE:
<223> OTHER INFORMATION: Nucleic acid sequence for encoding igHER2 light chain-(S4G)3-Zb1

<400> SEQUENCE: 15

```
gacatccaga tgacccagtc ccctccagc ctgtctgcct ctgtgggcga cagagtgacc      60
atcacctgtc gggcctccca ggacgtgaac accgccgtgg cttggtatca gcagaagccc    120
ggcaaggccc ccaagctgct gatctactcc gcctccttcc tgtactccgg cgtgccctcc    180
agattctccg gctccagatc tggcaccgac ttcaccctga ccatctccag cctgcagccc    240
```

```
gaggacttcg ccacctacta ctgccagcag cactacacca ccccccctac ctttggccag      300
ggcaccaagg tggaaatcaa gcggaccgtg gccgctccct ccgtgttcat cttcccacct      360
tccgacgagc agctgaagtc cggcaccgcc tctgtcgtgt gcctgctgaa caacttctac      420
ccccgcgagg ccaaggtgca gtggaaggtg gacaatgccc tgcagtccgg caactcccag      480
gaatccgtca ccgagcagga ctccaaggac agcacctact ccctgtcctc caccctgacc      540
ctgtccaagg ccgactacga gaagcacaag gtgtacgcct gcgaagtgac ccaccagggc      600
ctgtccagcc ccgtgaccaa gtccttcaac cggggcgagt gc                        642
```

<210> SEQ ID NO 16
<211> LENGTH: 214
<212> TYPE: PRT
<213> ORGANISM: Artificial Sequence
<220> FEATURE:
<223> OTHER INFORMATION: Amino acid sequence of igHER2 light
      chain-(S4G)3-Zb1

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 17
<211> LENGTH: 975
<212> TYPE: DNA
<213> ORGANISM: Artificial Sequence
<220> FEATURE:
<223> OTHER INFORMATION: Nucleic acid sequence for encoding
      scCD19-(S4G)3-Zb1

<400> SEQUENCE: 17

```
gaggtgcagc tgttggagtc tgggggaggc ttggtacagc ctgggggtc cctgagactc     60 tcctgtgcag cctctggatt cacctttagc gattattata tgagctgggt ccgccaggct    120
ccagggaagg ggctggagtg ggtctcaggg atctattatg atggttcggc taagtattac    180
gctgattctg taaaaggtcg gttcaccatc tccagagaca attccaagaa cacgctgtat    240
ctgcaaatga acagcctgag agccgaggac acggccgtgt attactgtgc gaaaggtcct    300 aattttgta atgatcggac ttgttcttat tattatgcta tggacgtctg gggccagggt    360
acactggtca ccgtgagctc aggtggaggc ggttcaggcg gaggtggatc cggcggtggc    420
ggatcgcagt ctgtgctgac tcagccaccc tcagcgtctg gaccccccgg cagagggtc    480 accatctctt gttatggtca gccgtctaat attggcagta atgctgtcta ctggtaccag    540
cagctaccag gaacggcccc caaactcctc atctatgatg ataatcatcg gccaagcggg    600
gtccctgacc gattctctgg ctccaagtct ggcacctcag cctccctggc catcagtggg    660
ctccggtccg aggatgaggc tgattattac tgtggtacct gggattatag cctgagtggt    720
tatgtcttag gcggaggcac caagctgacg gtcctatcat caagcagtgg aagttcttca    780
tccggctcat catcttcagg tgtcgataac aaattcaaca agagctgggc tgggctacc    840 tgggagattt ttaatcttcc gaatttaaac ggtgttcaag tgaaagcttt tatcgatagc    900
ctgcgcgacg atcctagcca gagcgcaaat ttgctggccg aagcaaaaaa actgaatgat    960
gcgcaggcgc caaag                                                     975

<210> SEQ ID NO 18
<211> LENGTH: 325
<212> TYPE: PRT
<213> ORGANISM: Artificial Sequence
<220> FEATURE:
<223> OTHER INFORMATION: Amino acid sequence of scCD19-(S4G)3-Zb1

<400> SEQUENCE: 18

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Ser Ala Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Asn Phe Cys Asn Asp Arg Thr Cys Ser Tyr Tyr Tyr
            100                 105                 110

Ala Met Asp Val Trp Gly Gln Gly Thr Leu Val Thr Val Ser Ser Gly
        115                 120                 125

Gly Gly Gly Ser Gly Gly Gly Gly Ser Gly Gly Gly Gly Ser Gln Ser
    130                 135                 140

Val Leu Thr Gln Pro Pro Ser Ala Ser Gly Thr Pro Gly Gln Arg Val
145                 150                 155                 160

Thr Ile Ser Cys Tyr Gly Gln Pro Ser Asn Ile Gly Ser Asn Ala Val
                165                 170                 175

Tyr Trp Tyr Gln Gln Leu Pro Gly Thr Ala Pro Lys Leu Leu Ile Tyr
            180                 185                 190
```

-continued

```
Asp Asp Asn His Arg Pro Ser Gly Val Pro Asp Arg Phe Ser Gly Ser
        195                 200                 205

Lys Ser Gly Thr Ser Ala Ser Leu Ala Ile Ser Gly Leu Arg Ser Glu
        210                 215                 220

Asp Glu Ala Asp Tyr Tyr Cys Gly Thr Trp Asp Tyr Ser Leu Ser Gly
225                 230                 235                 240

Tyr Val Leu Gly Gly Gly Thr Lys Leu Thr Val Leu Ser Ser Ser Ser
                245                 250                 255

Gly Ser Ser Ser Ser Gly Ser Ser Ser Gly Val Asp Asn Lys Phe
            260                 265                 270

Asn Lys Glu Leu Gly Trp Ala Thr Trp Glu Ile Phe Asn Leu Pro Asn
        275                 280                 285

Leu Asn Gly Val Gln Val Lys Ala Phe Ile Asp Ser Leu Arg Asp Asp
        290                 295                 300

Pro Ser Gln Ser Ala Asn Leu Leu Ala Glu Ala Lys Lys Leu Asn Asp
305                 310                 315                 320

Ala Gln Ala Pro Lys
            325

<210> SEQ ID NO 19
<211> LENGTH: 975
<212> TYPE: DNA
<213> ORGANISM: Artificial Sequence
<220> FEATURE:
<223> OTHER INFORMATION: Nucleic acid sequence for encoding
      scCD19-(G4S)3-Zb1

<400> SEQUENCE: 19
gaggtgcagc tgttggagtc tgggggaggc ttggtacagc ctgggggtc cctgagactc        60 tcctgtgcag cctctggatt caccttttagc gattattata tgagctgggt ccgccaggct      120
ccagggaagg gctgagtg gtctcaggg atctattatg atggttcggc taagtattac         180
gctgattctg taaaaggtcg gttcaccatc tccagagaca attccaagaa cacgctgtat      240
ctgcaaatga acagcctgag agccgaggac acggccgtgt attactgtgc gaaaggtcct      300
aatttttgta atgatcggac ttgttcttat tattatgcta tggacgtctg gggccagggt      360
acactggtca ccgtgagctc aggtggaggc ggttcaggcg aggtggatc cggcggtggc      420 ggatcgcagt ctgtgctgac tcagccaccc tcagcgtctg gaccccccgg cagagggtc      480 accatctctt gttatggtca gccgtctaat attggcagta atgctgtcta ctggtaccag      540
cagctaccag gaacggcccc caaactcctc atctatgatg ataatcatcg gccaagcggg      600
gtccctgacc gattctctgg ctccaagtct ggcacctcag cctccctggc catcagtggg      660
ctccggtccg aggatgaggc tgattattac tgtggtacct gggattatag cctgagtggt      720
tatgtcttag gcggaggcac caagctgacg gtcctaggtg aggtggtag tggtggtggt      780 ggtagtggtg gtgaggtag tgtcgataac aaattcaaca agagctggg ctgggctacc      840 tgggagattt ttaatcttcc gaatttaaac ggtgttcaag tgaaagcttt tatcgatagc      900
ctgcgcgacg atcctagcca gagcgcaaat ttgctggccg aagcaaaaaa actgaatgat      960
gcgcaggcgc caaag                                                     975

<210> SEQ ID NO 20
<211> LENGTH: 325
<212> TYPE: PRT
<213> ORGANISM: Artificial Sequence
<220> FEATURE:
```

<223> OTHER INFORMATION: Amino acid sequence of scCD19-(G4S)3-Zb1

<400> SEQUENCE: 20

```
Glu Val Gln Leu Leu Glu Ser Gly Gly Gly Leu Val Gln Pro Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Ser Ala Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Asn Phe Cys Asn Asp Arg Thr Cys Ser Tyr Tyr Tyr
            100                 105                 110

Ala Met Asp Val Trp Gly Gln Gly Thr Leu Val Thr Val Ser Ser Gly
        115                 120                 125

Gly Gly Gly Ser Gly Gly Gly Gly Ser Gly Gly Gly Gly Ser Gln Ser
    130                 135                 140

Val Leu Thr Gln Pro Pro Ser Ala Ser Gly Thr Pro Gly Gln Arg Val
145                 150                 155                 160

Thr Ile Ser Cys Tyr Gly Gln Pro Ser Asn Ile Gly Ser Asn Ala Val
                165                 170                 175

Tyr Trp Tyr Gln Gln Leu Pro Gly Thr Ala Pro Lys Leu Leu Ile Tyr
            180                 185                 190

Asp Asp Asn His Arg Pro Ser Gly Val Pro Asp Arg Phe Ser Gly Ser
        195                 200                 205

Lys Ser Gly Thr Ser Ala Ser Leu Ala Ile Ser Gly Leu Arg Ser Glu
    210                 215                 220

Asp Glu Ala Asp Tyr Tyr Cys Gly Thr Trp Asp Tyr Ser Leu Ser Gly
225                 230                 235                 240

Tyr Val Leu Gly Gly Gly Thr Lys Leu Thr Val Leu Gly Gly Gly Gly
                245                 250                 255

Ser Gly Gly Gly Gly Ser Gly Gly Gly Gly Ser Val Asp Asn Lys Phe
            260                 265                 270

Asn Lys Glu Leu Gly Trp Ala Thr Trp Glu Ile Phe Asn Leu Pro Asn
        275                 280                 285

Leu Asn Gly Val Gln Val Lys Ala Phe Ile Asp Ser Leu Arg Asp Asp
    290                 295                 300

Pro Ser Gln Ser Ala Asn Leu Leu Ala Glu Ala Lys Lys Leu Asn Asp
305                 310                 315                 320

Ala Gln Ala Pro Lys
                325
```

<210> SEQ ID NO 21
<211> LENGTH: 975
<212> TYPE: DNA
<213> ORGANISM: Artificial Sequence
<220> FEATURE:
<223> OTHER INFORMATION: Nucleic acid sequence for encoding scCD19-(S4G)3-Zb2

<400> SEQUENCE: 21
gaggtgcagc tgttggagtc tgggggaggc ttggtacagc ctggggggtc cctgagactc    60

```
tcctgtgcag cctctggatt cacctttagc gattattata tgagctgggt ccgccaggct    120
ccagggaagg ggctggagtg ggtctcaggg atctattatg atggttcggc taagtattac    180
gctgattctg taaaaggtcg gttcaccatc tccagagaca attccaagaa cacgctgtat    240
ctgcaaatga acagcctgag agccgaggac acggccgtgt attactgtgc gaaaggtcct    300 aattttgta atgatcggac ttgttcttat tattatgcta tggacgtctg gggccagggt    360
acactggtca ccgtgagctc aggtggaggc ggttcaggcg gaggtggatc cggcggtggc    420
ggatcgcagt ctgtgctgac tcagccaccc tcagcgtctg gaccccggg cagagggtc    480 accatctctt gttatggtca gccgtctaat attggcagta atgctgtcta ctggtaccag    540
cagctaccag gaacggcccc caaactcctc atctatgatg ataatcatcg gccaagcggg    600
gtccctgacc gattctctgg ctccaagtct ggcacctcag cctccctggc catcagtggg    660
ctccggtccg aggatgaggc tgattattac tgtggtacct gggattatag cctgagtggt    720
tatgtcttag gcggaggcac caagctgacg gtcctatcat caagcagtgg aagttcttca    780
tccggctcat catcttcagg tgtcgataac aaattcaaca agagcgcgt aattgcaatc    840 ggtgaaatta tgcgtctgcc aaacctgaat agcctgcagg ttgtggcctt tataaactct    900
ctgcgcgatg acccgagtca gtcagcaaac ctgcttgcgg aagcgaaaaa gctgaatgat    960
gcccaagctc ctaaa                                                     975

<210> SEQ ID NO 22
<211> LENGTH: 325
<212> TYPE: PRT
<213> ORGANISM: Artificial Sequence
<220> FEATURE:
<223> OTHER INFORMATION: Amino acid sequence of scCD19-(S4G)3-Zb2

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Ser Ala Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Asn Phe Cys Asn Asp Arg Thr Cys Ser Tyr Tyr Tyr
            100                 105                 110

Ala Met Asp Val Trp Gly Gln Gly Thr Leu Val Thr Val Ser Ser Gly
        115                 120                 125

Gly Gly Gly Ser Gly Gly Gly Ser Gly Gly Gly Ser Gln Ser
    130                 135                 140

Val Leu Thr Gln Pro Pro Ser Ala Ser Gly Thr Pro Gly Gln Arg Val
145                 150                 155                 160

Thr Ile Ser Cys Tyr Gly Gln Pro Ser Asn Ile Gly Ser Asn Ala Val
                165                 170                 175

Tyr Trp Tyr Gln Gln Leu Pro Gly Thr Ala Pro Lys Leu Leu Ile Tyr
            180                 185                 190
```

Asp Asp Asn His Arg Pro Ser Gly Val Pro Asp Arg Phe Ser Gly Ser
            195                 200                 205

Lys Ser Gly Thr Ser Ala Ser Leu Ala Ile Ser Gly Leu Arg Ser Glu
    210                 215                 220

Asp Glu Ala Asp Tyr Tyr Cys Gly Thr Trp Asp Tyr Ser Leu Ser Gly
225                 230                 235                 240

Tyr Val Leu Gly Gly Gly Thr Lys Leu Thr Val Leu Ser Ser Ser Ser
                245                 250                 255

Gly Ser Ser Ser Ser Gly Ser Ser Ser Gly Val Asp Asn Lys Phe
            260                 265                 270

Asn Lys Glu Arg Val Ile Ala Ile Gly Glu Ile Met Arg Leu Pro Asn
    275                 280                 285

Leu Asn Ser Leu Gln Val Val Ala Phe Ile Asn Ser Leu Arg Asp Asp
    290                 295                 300

Pro Ser Gln Ser Ala Asn Leu Leu Ala Glu Ala Lys Lys Leu Asn Asp
305                 310                 315                 320

Ala Gln Ala Pro Lys
            325

<210> SEQ ID NO 23
<211> LENGTH: 975
<212> TYPE: DNA
<213> ORGANISM: Artificial Sequence
<220> FEATURE:
<223> OTHER INFORMATION: Nucleic acid sequence for encoding
      scCD19-(G4S)3-Zb2

<400> SEQUENCE: 23

| | | |
|---|---|---|
| gaggtgcagc tgttggagtc tgggggaggc ttggtacagc ctgggggtc cctgagactc | 60 |
| tcctgtgcag cctctggatt cacctttagc gattattata tgagctgggt ccgccaggct | 120 |
| ccagggaagg gctggagtg gtctcaggg atctattatg atggttcggc taagtattac | 180 |
| gctgattctg taaaaggtcg gttcaccatc tccagagaca attccaagaa cacgctgtat | 240 |
| ctgcaaatga acagcctgag agccgaggac acggccgtgt attactgtgc gaaaggtcct | 300 |
| aattttttgta atgatcggac ttgttcttat tattatgcta tggacgtctg gggccagggt | 360 |
| acactggtca ccgtgagctc aggtggaggc ggttcaggcg gaggtggatc cggcggtggc | 420 |
| ggatcgcagt ctgtgctgac tcagccaccc tcagcgtctg gaccccggg cagagggtc | 480 |
| accatctctt gttatggtca gccgtctaat attggcagta atgctgtcta ctggtaccag | 540 |
| cagctaccag gaacggcccc caaactcctc atctatgatg ataatcatcg gccaagcggg | 600 |
| gtccctgacc gattctctgg ctccaagtct ggcacctcag cctccctggc catcagtggg | 660 |
| ctccggtccg aggatgaggc tgattattac tgtggtacct gggattatag cctgagtggt | 720 |
| tatgtcttag gcggaggcac caagctgacg gtcctaggtg gaggtggtag tggtggtggt | 780 |
| ggtagtggtg gtgaggtag tgtcgataac aaattcaaca agagcgcgt aattgcaatc | 840 |
| ggtgaaatta tgcgtctgcc aaacctgaat agcctgcagg ttgtggcctt tataaactct | 900 |
| ctgcgcgatg acccgagtca gtcagcaaac ctgcttgcgg aagcgaaaaa gctgaatgat | 960 |
| gcccaagctc ctaaa | 975 |

<210> SEQ ID NO 24
<211> LENGTH: 325
<212> TYPE: PRT
<213> ORGANISM: Artificial Sequence
<220> FEATURE:
<223> OTHER INFORMATION: Amino acid sequence of scCD19-(G4S)3-Zb2

<400> SEQUENCE: 24

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Val Arg Gln Ala Pro Gly Lys Gly Leu Glu Trp Val
        35                  40                  45

Ser Gly Ile Tyr Tyr Asp Gly Ser Ala Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Gly Pro Asn Phe Cys Asn Asp Arg Thr Cys Ser Tyr Tyr Tyr
            100                 105                 110

Ala Met Asp Val Trp Gly Gln Gly Thr Leu Val Thr Val Ser Ser Gly
        115                 120                 125

Gly Gly Gly Ser Gly Gly Gly Ser Gly Gly Gly Ser Gln Ser
    130                 135                 140

Val Leu Thr Gln Pro Pro Ser Ala Ser Gly Thr Pro Gly Gln Arg Val
145                 150                 155                 160

Thr Ile Ser Cys Tyr Gly Gln Pro Ser Asn Ile Gly Ser Asn Ala Val
                165                 170                 175

Tyr Trp Tyr Gln Gln Leu Pro Gly Thr Ala Pro Lys Leu Leu Ile Tyr
            180                 185                 190

Asp Asp Asn His Arg Pro Ser Gly Val Pro Asp Arg Phe Ser Gly Ser
            195                 200                 205

Lys Ser Gly Thr Ser Ala Ser Leu Ala Ile Ser Gly Leu Arg Ser Glu
210                 215                 220

Asp Glu Ala Asp Tyr Tyr Cys Gly Thr Trp Asp Tyr Ser Leu Ser Gly
225                 230                 235                 240

Tyr Val Leu Gly Gly Gly Thr Lys Leu Thr Val Leu Gly Gly Gly Gly
                245                 250                 255

Ser Gly Gly Gly Gly Ser Gly Gly Gly Gly Ser Val Asp Asn Lys Phe
            260                 265                 270

Asn Lys Glu Arg Val Ile Ala Ile Gly Glu Ile Met Arg Leu Pro Asn
            275                 280                 285

Leu Asn Ser Leu Gln Val Val Ala Phe Ile Asn Ser Leu Arg Asp Asp
        290                 295                 300

Pro Ser Gln Ser Ala Asn Leu Leu Ala Glu Ala Lys Lys Leu Asn Asp
305                 310                 315                 320

Ala Gln Ala Pro Lys
            325

<210> SEQ ID NO 25
<211> LENGTH: 174
<212> TYPE: DNA
<213> ORGANISM: Artificial Sequence
<220> FEATURE:
<223> OTHER INFORMATION: Nucleic acid sequence for encoding
      Codon-optimized Zb2

<400> SEQUENCE: 25
gtcgataaca aattcaataa ggaacgcgtg attgccattg gcgagatcat cgcgcctgccc       60 aatctgaata gcttgcaggt ggtggccttt atcaactccc ttcgggatga cccatcacag    120
tctgccaacc tcctggctga ggcaaagaag ctcaacgacg cgcaggctcc taaa          174

<210> SEQ ID NO 26
<211> LENGTH: 58
<212> TYPE: PRT
<213> ORGANISM: Artificial Sequence
<220> FEATURE:
<223> OTHER INFORMATION: Amino acid sequence of Codon-optimized Zb2

<400> SEQUENCE: 26

Val Asp Asn Lys Phe Asn Lys Glu Arg Val Ile Ala Ile Gly Glu Ile
1               5                   10                  15

Met Arg Leu Pro Asn Leu Asn Ser Leu Gln Val Val Ala Phe Ile Asn
                20                  25                  30

Ser Leu Arg Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 27
<211> LENGTH: 672
<212> TYPE: DNA
<213> ORGANISM: Artificial Sequence
<220> FEATURE:
<223> OTHER INFORMATION: Nucleic acid sequence for encoding CAR
      construct (CD8 hinge-TM-CD137-CD3z)

<400> SEQUENCE: 27
accacaactc cagctccccg gcccccctacc cctgcaccaa caatcgccag ccagcctctg     60
tccctgagac cagaggcatg taggccagct gcaggaggag cagtgcatac aagaggcctg    120
gacttcgcct gcgatatcta catttgggct cctctggcag gaacttgtgg cgtgctgctg    180
ctgtctctgg tcatcaccct gtactgcaaa aggggccgca agaaactgct gtatattttc    240
aagcagccct tcatgcggcc cgtgcagacc acacaggagg aagacgggtg ctcctgtaga    300
ttccccgagg aagaggaagg cgggtgtgag ctgcgcgtca agttcagccg atcagccgat    360
gctcctgcat acaagcaggg ccagaatcag ctgtataacg agctgaatct ggggcgccga    420
gaggaatacg acgtgctgga taagcggaga gggagggacc ccgaaatggg aggcaaacct    480
aggcgcaaga acccacagga gggactgtac aatgaactgc agaaggacaa atggccgag     540 gcttattccg aaattgggat gaaaggagag cgacggagag ggaagggaca cgatgggctg    600
tatcagggac tgtctaccgc cactaaagat acctacgacg ctctgcacat gcaggctctg    660
ccacctcgct ga                                                       672

<210> SEQ ID NO 28
<211> LENGTH: 223
<212> TYPE: PRT
<213> ORGANISM: Artificial Sequence
<220> FEATURE:
<223> OTHER INFORMATION: Amino acid sequence of CAR construct (CD8
      hinge-TM-CD137-CD3z)

<400> SEQUENCE: 28

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile

```
                    35                  40                  45
Trp Ala Pro Leu Ala Gly Thr Cys Gly Val Leu Leu Leu Ser Leu Val
                50                  55                  60

Ile Thr Leu Tyr Cys Lys Arg Gly Arg Lys Lys Leu Leu Tyr Ile Phe
 65                  70                  75                  80

Lys Gln Pro Phe Met Arg Pro Val Gln Thr Thr Gln Glu Glu Asp Gly
                85                  90                  95

Cys Ser Cys Arg Phe Pro Glu Glu Glu Gly Gly Cys Glu Leu Arg
                100                 105                 110

Val Lys Phe Ser Arg Ser Ala Asp Ala Pro Ala Tyr Lys Gln Gly Gln
                115                 120                 125

Asn Gln Leu Tyr Asn Glu Leu Asn Leu Gly Arg Arg Glu Glu Tyr Asp
                130                 135                 140

Val Leu Asp Lys Arg Arg Gly Arg Asp Pro Glu Met Gly Gly Lys Pro
145                 150                 155                 160

Arg Arg Lys Asn Pro Gln Glu Gly Leu Tyr Asn Glu Leu Gln Lys Asp
                165                 170                 175

Lys Met Ala Glu Ala Tyr Ser Glu Ile Gly Met Lys Gly Glu Arg Arg
                180                 185                 190

Arg Gly Lys Gly His Asp Gly Leu Tyr Gln Gly Leu Ser Thr Ala Thr
                195                 200                 205

Lys Asp Thr Tyr Asp Ala Leu His Met Gln Ala Leu Pro Pro Arg
                210                 215                 220

<210> SEQ ID NO 29
<211> LENGTH: 21
<212> TYPE: PRT
<213> ORGANISM: Artificial Sequence
<220> FEATURE:
<223> OTHER INFORMATION: Amino acid sequence of CD8 leader

<400> SEQUENCE: 29

Met Ala Leu Pro Val Thr Ala Leu Leu Leu Pro Leu Ala Leu Leu Leu
  1               5                  10                  15

His Ala Ala Arg Pro
                20
```

SWITCH MOLECULE AND SWITCHABLE CHIMERIC ANTIGEN RECEPTOR

CROSS-REFERENCE TO RELATED APPLICATIONS

This application is a national phase application of PCT Application No. PCT/KR2019/004720, filed on Apr. 18, 2019, which claims priority to Korean Patent Application No. 10-2018-0045228, filed on Apr. 18, 2018. The entire disclosures of the applications identified in this paragraph are incorporated herein by references.

FIELD

The present invention relates to a switch molecule for activating a chimeric antigen receptor-effector cell, to a polypeptide or fusion protein binding thereto, and to a chimeric antigen receptor.

BACKGROUND

Recent clinical studies of chimeric antigen receptor T (CAR-T) cells in patients with B-cell malignancies have demonstrated sustained remissions. CARs endow patient-derived T cells with the ability to recognize and eliminate cancer cells through a surface-displayed single-chain antibody variable domain (scFv) coupled to intracellular costimulatory and activation domains. By linking the specificity of antibody recognition with T-cell-mediated cytotoxicity, CAR-T cells are highly efficacious against antigen-positive tumor cells in a human lymphocyte antigen (HLA)-independent manner. Thus far, the greatest clinical successes have been achieved by targeting the pan-B-cell antigen CD19 (CART-19) in patients with relapsed refractory acute lymphoblastic leukemia (ALL). The success of CART-19 in treating patients who have previously failed treatment with the CD19 bispecific blinatumomab highlights the benefits of genetic engineering approaches that enhance the cellular immune response to tumors.

In spite of impressive success in early-stage clinical trials, conventional CAR-T cells have limitations associated with the lack of control over their activation and expansion in vivo. For example, CAR-T cells undergo rapid proliferation up to $10^4$-fold expansion upon encountering antigen-positive cells in the patient, which has resulted in serious cases of tumor lysis syndrome (TLS) and fatal cytokine release syndrome (CRS). Additional complications may be caused by the persistent on-target activity of CAR-T cells. For example, in the case of CART-19, engineered T cells indiscriminately kill malignant and normal B cells, leading to long-term B-cell aplasia. Finally, the fixed antigen-specificity of conventional CAR-T cells precludes the targeting of antigen-loss escape mutants, which has recently been shown to be a source of relapse in up to 10% of ALL patients undergoing CART-19 therapy.

Therefore, there is an increasing demand for development of a switch molecule that can control the activity of CAR-T cells upon the appearance of severe toxicity and can mediate interaction between CAR-T cells and target cells upon the mutation of the antigen in order to enhance the safety of CAR-T cells.

SUMMARY

Technical Problem

Leading to the present invention, intensive and through research, conducted by the present inventors, into a novel switch molecule capable of controlling the activity of CAR-T cells and mediating interaction between CAR-T cells and target cells resulted in the finding that affibodies binding specifically to each other to form a pair (Zb pair) can be used as a switch molecule and a CAR.

A purpose of the present invention is to provide a switch molecule for activating a chimeric antigen receptor-effector cell.

Another purpose of the present invention is to provide (a) a switch molecule for activating a chimeric antigen receptor-effector cell and (b) a polypeptide or fusion protein binding specifically to switch molecule.

A further purpose of the present invention is to provide a chimeric antigen receptor (CAR) comprising a switch molecule or a fusion protein.

Technical Solution

The present disclosure provides the method as set forth in the following 1 to 47.

1. A switch molecule for activating a chimeric antigen receptor-effector cell, the molecule comprising:
   (a) a targeting moiety binding to a cell surface molecule on a target cell; and
   (b) a polypeptide binding to a chimeric antigen receptor (CAR) on the effector cell.

2. The switch molecule as set forth in 1, wherein (a) the targeting moiety is an antibody, an antigen-binding fragment of an antibody, or a target-binding polypeptide.

3. The switch molecule as set forth in 2, wherein the antibody is selected from the group consisting of a monoclonal antibody, a polyclonal antibody, a synthetic antibody, a human antibody, a humanized antibody, a single domain antibody, and a single chain variable fragment.

4. The switch molecule as set forth in 1 to 3, wherein the activation of the effector cell results in cytotoxicity against a target cell, cytokine secretion, or a combination thereof.

5. The switch molecule of 1 to 4, wherein the effector cell is selected from the group consisting of a dendritic cell, a killer dendritic cell, a mast cell, a natural killer cell, a B lymphocyte, a T lymphocyte, a macrophage, and a precursor cell thereof.

6. The switch molecule of 1 to 5, wherein (a) the targeting moiety binds specifically to a HER2 or CD19 antigen.

7. The switch molecule as set forth in 1 to 5, wherein (a) the targeting moiety is a target-binding polypeptide that binds specifically to a HER2 antigen and which comprises the amino acid sequence comprising the $1^{st}$ to the $58^{th}$ amino acid residue on SEQ ID NO: 10.

8. The switch molecule as set forth in 1 to 5, wherein (a) the targeting moiety is an antibody or an antigen-binding fragment that binds specifically to a HER2 antigen and which comprises the amino acid sequence comprising the $1^{st}$ to the $243^{rd}$ amino acid residue on SEQ ID NO: 12.

9. The switch molecule as set forth in 1 to 5, wherein (a) the targeting moiety is an antibody or an antigen-binding fragment that binds specifically to a HER2 antigen and comprises the amino acid sequence comprising the $1^{st}$ to $119^{th}$ amino acid residue on SEQ ID NO: 14 as a heavy chain variable region and the amino acid sequence comprising the $1^{st}$ to the $107^{th}$ amino acid residue on SEQ ID NO: 16 as a light chain variable region.

10. The switch molecule as set forth in 1 to 5, wherein (a) the targeting moiety is an antibody or an antigen-binding fragment that binds specifically to a CD19 antigen and comprises the amino acid sequence comprising the $1^{st}$ to the $252^{nd}$ amino acid residue on SEQ ID NO: 18.

11. The switch molecule as set forth in 1 to 10, wherein (b) the polypeptide binding to a chimeric antigen receptor is an antibody, an antigen-binding fragment of an antibody, or a target-binding polypeptide.

12. The switch molecule as set forth in 1 to 11, wherein (b) the polypeptide binding to a chimeric antigen receptor on the effector cell is a target-binding polypeptide comprising the amino acid sequence comprising the $1^{st}$ to the $58^{th}$ amino acid residue on SEQ ID NO: 2.

13. The switch molecule as set forth in 1 to 11, wherein (b) the polypeptide binding to a chimeric antigen receptor on the effector cell is a target-binding polypeptide comprising the amino acid sequence comprising the $1^{st}$ to the $58^{th}$ amino acid residue on SEQ ID NO: 4.

14. The switch molecule as set forth in 1, wherein the switch molecule comprises the amino acid sequence of SEQ ID NO: 10.

15. The switch molecule as set forth in 1, wherein the amino acid sequence comprising the $74^{th}$ to the $131^{st}$ amino acid residue on SEQ ID NO: 10 is replaced by the amino acid sequence comprising the $1^{st}$ to the $58^{th}$ amino acid residue on SEQ ID NO: 4.

16. The switch molecule as set forth in 1, wherein the switch molecule comprises the amino acid sequence of SEQ ID NO: 12.

17. The switch molecule as set forth in 1, wherein the amino acid sequence comprising the $259^{th}$ to the $316^{th}$ amino acid residue on SEQ ID NO: 12 is replaced by the amino acid sequence comprising the $1^{st}$ to the $58^{th}$ amino acid sequence on SEQ ID NO: 4.

18. The switch molecule as set forth in 1, wherein the switch molecule comprises the amino acid sequence of SEQ ID NO: 14 and the amino acid sequence of SEQ ID NO: 16.

19. The switch molecule as set forth in 1, wherein the amino acid sequence comprising the $466^{th}$ to the $523^{rd}$ amino acid residue on the amino acid sequence of SEQ ID NO: 14 is replaced by the amino acid sequence comprising the $1^{st}$ to the $58^{th}$ amino acid residue on SEQ ID NO: 4.

20. The switch molecule as set forth in 1, wherein the switch molecule comprises the amino acid sequence of SEQ ID NO: 18, 20, 22, or 24.

21. A composition, comprising the switch molecule of any one of 1 to 20.

22. An immunotherapeutic pharmaceutical composition, comprising the switch molecule of any of 1 to 20 and a pharmaceutically acceptable carrier.

23. A complex, comprising:
(a) a switch molecule for activating a chimeric antigen receptor-effector cell, the molecule comprising:
(aa) a targeting moiety binding to a cell surface molecule on a target cell; and
(bb) a polypeptide binding to a chimeric antigen receptor on the effector cell; and
(b) a polypeptide or fusion protein binding specifically to the switch molecule.

24. The complex as set forth in 23, wherein (a) the switch molecule is the switch molecule as set forth in any one of 1 to 20.

25. The complex as set forth in 23, wherein (aa) the targeting moiety is an antibody, an antigen-binding fragment of an antibody, or a target-binding polypeptide.

26. The complex as set forth in 23, wherein (bb) the polypeptide binding to a chimeric antigen receptor is an antibody, an antigen-binding fragment of an antibody, or a target-binding polypeptide.

27. The complex as set forth in 23, wherein (b) the polypeptide or fusion protein is an antibody, an antigen-binding fragment of an antibody, a target-binding polypeptide, or a chimeric antigen receptor comprising thereof, which each target the switch molecule.

28. A chimeric antigen receptor (CAR), comprising:
(aa) an extracellular domain comprising an antibody, an antigen-binding fragment of an antibody, or a target-binding polypeptide, which targets the switch molecule as set forth in any one of 1 to 20;
(bb) a transmembrane domain; and
(cc) an intracellular signaling domain.

29. The chimeric antigen receptor as set forth in 28, wherein the intracellular signaling domain is an intracellular signaling domain in a stimulatory molecule or a costimulatory molecule.

30. The chimeric antigen receptor as set forth in 28 or 29, wherein (bb) the transmembrane domain is a transmembrane domain of a protein selected from the group consisting of the alpha, beta, or zeta chain of a T-cell receptor, CD27, CD28, CD3, epsilon, CD45, CD4, CD5, CD8(CD8a), CD9, CD16, CD22, CD33, CD37, CD64, CD80, CD86, CD134, CD137, and CD154.

31. The chimeric antigen receptor as set forth in any one of 28 to 30, wherein (cc) the intracellular signaling domain is a domain derived from the CD3ζ(CD3 zeta) chain.

32. The chimeric antigen receptor as set forth in any one of 28 to 31, wherein (cc) the intracellular signaling domain further comprises a costimulatory molecule selected from the group consisting of OX40 (CD134), CD2, CD27, CD28, CDS, ICAM-1, LFA-1(CD11a/CD18), and 4-1BB (CD137).

33. An effector cell expressing a chimeric antigen receptor, wherein the chimeric antigen receptor targets (b) the polypeptide binding to a chimeric antigen receptor in the switch molecule as set forth in any one of 1 to 20.

34. The effector cell as set forth in 33, wherein the effector cell is selected from the group consisting of a dendritic cell, a killer dendritic cell, a mast cell, a natural killer cell, a B lymphocyte, a T lymphocyte, a macrophage, and a precursor cell thereof.

35. The effector cell as set forth in 34, wherein the T lymphocyte is selected from an inflammatory T lymphocyte, a cytotoxic T lymphocyte, a regulatory T lymphocyte, and a helper T lymphocyte.

36. A method, comprising a step of administering, to a subject that needs to be treated, an effector cell expressing the chimeric antigen receptor as set forth in any one of 29 to 32, and the switch molecule binding to the chimeric antigen receptor as set forth any one of 1 to 20.

37. The method as set forth in 36, further comprising a step of additionally administering to the subject at least one switch molecule that is different from the previously administered switch molecule and binds to a cell surface molecule on a target cell.

38. The method as set forth in 36 or 37, the method is a method for treating a disease or condition associated with tumors or cancer.

39. The method as set forth in 36 or 37, the method is a method for treating a disease or condition associated with autoimmunity.

40. A method for restraining activity of a chimeric antigen receptor-expressing effector cell (CAR-effector cell) in a subject in need thereof, the method comprising the steps of:
(a) administering to the subject an effector cell expressing the chimeric antigen receptor as set forth in 25 and the switch molecule binding to the chimeric antigen receptor as set forth in any one of claims 1 to 20; and
(b) additionally administering to the subject a polypeptide binding to the chimeric antigen receptor on the effector.

41. chimeric antigen receptor-effector cell therapeutic system, comprising: the switch molecule as set forth in any one of 1 to 20; and a chimeric antigen receptor targeting the switch molecule.

42. A nucleic acid molecule encoding the switch molecule as set forth in any one of 1 to 20.

43. A nucleic acid molecule encoding the complex as set forth in any one of 23 to 27.

44. A nucleic acid molecule encoding the chimeric antigen receptor as set forth in any one of 28 to 32.

45. A recombinant vector carrying the nucleic acid molecule as set forth in any one of 42 to 44.

46. A host cell transformed with the recombinant vector as set forth in 45.

47. A method comprising a step of culturing the host cell as set forth in 46.

According to an aspect thereof, the present invention provides a switch molecule for activating a chimeric antigen receptor-effector cell, the switch molecule comprising:

(a) a targeting moiety binding to a cell surface molecule on a target cell; and (b) a polypeptide binding to a chimeric antigen receptor on the effector cell.

According to an embodiment of the present invention, (a) the targeting moiety is a target-binding polypeptide such as an antibody, an antigen-binding fragment of an antibody, or affibody.

According to an exemplary embodiment of the present invention, (a) the targeting moiety is a target-binding polypeptide that binds specifically to a HER2 antigen and which comprises the amino acid sequence comprising the $1^{st}$ to the $58^{th}$ amino acid residue on SEQ ID NO: 10. The amino acid sequence comprising the $1^{st}$ to the $58^{th}$ amino acid residue on SEQ ID NO: 10 may be encoded by the nucleotide sequence comprising the $1^{st}$ to the $174^{th}$ base on SEQ ID NO: 9, but is not limited thereto.

According to another exemplary embodiment of the present invention, (a) the targeting moiety is an antibody or an antigen-binding fragment that binds specifically to a HER2 antigen and which comprises the amino acid sequence comprising the $1^{st}$ to the $243^{rd}$ amino acid residue on SEQ ID NO: 12. the amino acid sequence comprising the $1^{st}$ to the $243^{rd}$ amino acid residue on SEQ ID NO: 12 may be encoded by the nucleotide sequence comprising the $1^{st}$ to the $729^{th}$ base on SEQ ID NO: 11, but is not limited thereto.

According to another exemplary embodiment of the present invention, (a) the targeting moiety is an antibody or an antigen-binding fragment that binds specifically to a HER2 antigen and comprises the amino acid sequence comprising the $1^{st}$ to $119^{th}$ amino acid residue on SEQ ID NO: 14 as a heavy chain variable region and the amino acid sequence comprising the $1^{st}$ to the $107^{th}$ amino acid residue on SEQ ID NO: 16 as a light chain variable region. The amino acid sequence comprising the $1^{st}$ to $119^{th}$ amino acid residue on SEQ ID NO: 14 may be encoded by the nucleotide sequence comprising the $1^{st}$ to the $357^{th}$ base on SEQ ID NO: 13 while the amino acid sequence comprising the $1^{st}$ to the $107^{th}$ amino acid residue on SEQ ID NO: 16 may be encoded by the nucleotide sequence comprising the $1^{st}$ to the $321^{st}$ base on SEQ ID NO: 15, but with no limitations thereto.

According to another embodiment of the present invention, (b) the polypeptide binding to the chimeric antigen receptor is a target-binding polypeptide, such as an antibody, an antigen-binding fragment, or affibody.

According to an exemplary embodiment of the present invention, (b) the polypeptide binding to a chimeric antigen receptor on the effector cell is a target-binding polypeptide comprising the amino acid sequence comprising the $1^{st}$ to the $58^{th}$ amino acid residue on SEQ ID NO: 2. The amino acid sequence comprising the $1^{st}$ to the $58^{th}$ amino acid residue on SEQ ID NO: 2 may be encoded by the nucleotide sequence comprising the $1^{st}$ to the $174^{th}$ base on SEQ ID NO: 1, but is not limited thereto.

According to another exemplary embodiment of the present invention, (b) the polypeptide binding to a chimeric antigen receptor on the effector cell is a target-binding polypeptide comprising the amino acid sequence comprising the $1^{st}$ to the $58^{th}$ amino acid residue on SEQ ID NO: 4. The amino acid sequence comprising the $1^{st}$ to the $58^{th}$ amino acid residue on SEQ ID NO: 4 may be encoded by the nucleotide sequence comprising the $1^{st}$ to the $174^{th}$ base on SEQ ID NO: 3, but is not limited thereto.

According to a further exemplary embodiment of the present invention, the switch molecule comprises the amino acid sequence of SEQ ID NO: 10, and the amino acid sequence comprising the $74^{th}$ to the $131^{st}$ amino acid residue on SEQ ID NO: 10 may be replaced by the amino acid sequence comprising the $1^{st}$ to the $58^{th}$ amino acid residue on SEQ ID NO: 4. The amino acid sequence of SEQ ID NO: 10 may be encoded by the nucleotide sequence of SEQ ID NO: 9, but is not limited thereto.

According to another exemplary embodiment of the present invention, the switch molecule comprises the amino acid sequence of SEQ ID NO: 12, and the amino acid sequence comprising the $259^{th}$ to the $316^{th}$ amino acid residue on SEQ ID NO: 12 may be replaced by the amino acid sequence comprising the $1^{st}$ to the $58^{th}$ amino acid sequence on SEQ ID NO: 4. The amino acid sequence of SEQ ID NO: 12 may be encoded by the nucleotide sequence of SEQ ID NO: 11, but is not limited thereto.

According to a further exemplary embodiment of the present invention, the switch molecule comprises the amino acid sequence of SEQ ID NO: 14 and the amino acid sequence of SEQ ID NO: 16. The amino acid sequence comprising the $466^{th}$ to the $523^{rd}$ amino acid residue on the amino acid sequence of SEQ ID NO: 14 may be replaced by the amino acid sequence comprising the $1^{st}$ to the $58^{th}$ amino acid residue on SEQ ID NO: 4. The amino acid sequences of SEQ ID NOS: 14 and 16 may be encoded by the nucleotide sequences of SEQ ID NOS: 13 and 15, respectively, but are not limited thereto.

The term "antibody", as used herein, refers to an antibody specifically binding to a specific antigen and is intended to encompass not only a whole antibody but also an antigen-binding fragment thereof. A whole antibody includes two full-length light chains and two full-length heavy chains wherein the light chains are linked respectively to the heavy chains via disulfide bonds. The heavy chain constant regions are divided into isotypes of gamma (γ), mu (μ), alpha (α), delta (δ), and epsilon (ε), which are further divided into the subclasses gamma 1 (γ1), gamma 2 (γ2), gamma 3 (γ3), gamma 4 (γ4), alpha 1 (α1), and alpha 2 (α2). The light chain constant region is divided into kappa (κ) and lambda (λ) types (Cellular and Molecular Immunology, Wonsiewicz, M. J., Ed., Chapter 45, pp. 41-50, W. B. Saunders Co. Philadelphia, Pa. (1991); Nisonoff, A., Introduction to Molecular Immunology, $2^{nd}$ Ed., Chapter 4, pp. 45-65, Sinauer Associates, Inc., Sunderland, MA (1984)).

In this disclosure, the antibody includes an antibody selected from the group consisting of a monoclonal antibody, a polyclonal antibody, a synthetic antibody, a human antibody, a humanized antibody, a single domain antibody, and a single-chain variable fragment.

As used herein, the term "antigen-binding fragment" refers to a fragment having an antigen binding activity and is intended to encompass Fab, F(ab'), F(ab')2, and Fv. Of the antibody fragments, Fab (fragment antigen binding) is composed of one variable domain of each of the heavy and the light chain, one constant domain of the light chain, and the first constant domain (CH1) of the heavy chain, with one antigen-binding site retained therein. Fab' is different from Fab in that the former retains a hinge region which comprises at least one cysteine residue at C-terminal of the heavy chain CH1 domain. F(ab')2 is produced by forming a disulfide bond between cysteine residues in the hinge region of Fab'. Fv is a minimal antibody fragment composed only of variable regions of a heavy and a light chain and may be produced by a recombinant technology as disclosed in PCT International Patent Publication Nos. WO 88/10649, WO 88/106630, WO 88/07085, WO 88/07086, and WO 88/09344. In a two-chain Fv, variable regions of a light and a heavy chain are linked by a non-covalent bond. In a single-chin variable fragment (scFv), variable regions of a light and a heavy chain are linked by a covalent bond through a peptide linker or it may form a dimer structure like a two chain Fv through a direct linkage at the C-terminal. These antibody fragments are obtained through a proteinase treatment (for example, a whole antibody may be treated with a papain to obtain Fab or with a pepsin to obtain F(ab')2). Alternatively, a recombinant DNA technology may be employed to fabricate the antibody fragments.

According to an embodiment of the present invention, the antibody or the antigen-binding fragment may be in the form of Fab, scFv, or a whole antibody. In addition, the heavy chain constant domain may be any one selected from isotypes of gamma (γ), mu (μ), alpha (α), delta (δ), and epsilon (ε). The heavy chain constant domain is particularly an isotype of gamma 1 (IgG1), gamma 3 (IgG3), or gamma 4 (IgG4) and most particularly an isotype of gamma 1 (IgG1). The light chain constant domain is an isotype of kappa or lambda and particularly an isotype of kappa. Accordingly, the antibody of the present invention is in the form of Fab or ScFv composed of kappa (κ) light chain and gamma 1 (γ1) heavy chain or in the form of IgG1, but without limitations thereto.

The term "heavy chain", as used herein, refers to a full-length chain comprising three constant regions CH1, CH2, and CH3 and one variable region VH comprising an amino acid sequence which is sufficient for conferring specificity to an antigen as well as fragments thereof. also, the term "light chain, as used herein, refers to a full-length chain comprising one constant region CL and one variable region VL comprising an amino acid sequence which is sufficient for conferring specificity to an antigen as well as fragment thereof.

As used herein, the term "complementarity determining region" or "CDR" refers to an amino acid sequence of a hypervariable region within the heavy and light chain variable domains of an immunoglobulin (Kabat et al., Sequences of Proteins of Immunological Interest, $4^{th}$ Ed., U.S. Department of Health and Human Services, National Institutes of Health (1987)). There are three CDRs in each of the heavy chain (CDRH1, CDRH2, and CDRH3) and the light chain (CDRL1, CDRL2, and CDRL3). The CDRs provide major contact residues for binding to an antigen or an epitope.

By "humanized" forms of non-human (e.g., murine) antibodies are meant by chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. For the most part, humanized antibodies are human immunoglobulins (recipient antibody) in which residues from a complementary-determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, humanized antibodies can comprise residues which are found neither in the recipient antibody nor in the imported CDR or framework sequences. These modifications are made to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin sequence. The humanized antibody optimally also will comprise at least a portion of an immunoglobulin constant region (Fc), typically that of a human immunoglobulin.

Affibody® molecules are small proteins composed of 58 amino acid residues based on the Z domain, which is an affinity site for IgG in Protein A from *Staphylococcus aureus*. In this disclosure, "affibody" is also represented by "Z body" or "Zb". An affibody is a small protein composed of 58 amino acid residues. In protein sequencing of the affibody molecule, 13 amino acids that form the binding surface with IgG can bind to various target antigens depending on the amino acid sequence thereof and can be randomly arranged to construct libraries. Similar to antibodies, affibody molecules capable of binding to various target antigens can be screened from libraries through screening methods, such as phage display and yeast two hybrid (Y2H). Affibody molecules specifically binding to HER2 and amyloid-β have been recently developed using characteristics of affibody molecules capable of binding to target antigens (Orlova et al. 2006, Cancer Res., Gronwall et al., 2007, J. Biotechnol.). When administered into the human body, the affibody molecules are systemically diffused and fast removed through renal clearance because they have a very small molecular weight of 6 kDa, compared to IgG, which generally has a molecular weight of 150 kDa. Therefore, affibody molecules are mainly applied to the research and development of diagnostic specimens (Goldstein R et al., 2013, Expert Rev Anticancer Ther.). Affibody molecules have also been developed in the form of double antibodies binding to IgG (Yu F et al., 2014, MAbs). PCT Publication No. WO95/19374 discloses first-generation Z variant-based polypeptide scaffolds and PCT Publication No. WO2009/080811 discloses second-generation Z variant-based polypeptide scaffolds.

As used herein, the term "target-binding polypeptide" refers to a non-immunoglobulin polypeptide molecule which exhibits binding affinity for a target antigen or a hapten, like an antibody, but is not structurally relevant to an antibody. The target-binding polypeptides, also called antibody-like molecules or antibody mimetics, generally have a molecular weight of 3-20 kDa, unlike antibodies, which have a molecular weight of about 150 kDa. Examples of the target-binding polypeptide include, but are not limited to, an affibody derived from Z-domain of protein A, an affilin derived from gamma-B crystallin or ubiquitin, affimer derived from systatin, an affitin derived from Sac7d of Sulfolobus acidocaldarius, an alphabody derived from triple helix coiled coil, an anticalin derived from lipocalin, an avimer derived from a cell membrane receptor domain, DARPin derived from an ankyrin repeat motif, Fynomer derived from the SH3 domain of Fyn, a Kunits domain peptide derived from the Kunits domain of protease inhibitor, a monobody derived from the 10 th type III domain of fibronectin, and nanoCLAMP derived from carbohydrate binding module 32-2 of NagH in Clostridium perfringens. Through various screening methods known in the art, such as phage display, ribosome display, etc., the target-binding polypeptide may be engineered to have binding affinity for any target antigen or hapten.

The terms "antibody", "antigen-binding fragment", and "target-binding polypeptide" used below are as defined above.

The term "cancer" as used herein is defined as disease characterized by the rapid and uncontrolled growth of aberrant cells. Cancer cells can spread locally or through the bloodstream and lymphatic system to other parts of the body. Examples of cancer include solid tumors and non-solid tumors (e.g., hematological tumor).

The term "tumor" as used herein, refers to an abnormal growth of tissue that may be benign, pre-cancerous, malignant, or metastatic.

As used herein, the term "target-binding polypeptide" refers to a non-immunoglobulin polypeptide molecule which exhibits binding affinity for a target antigen or a hapten, like an antibody, but is structurally relevant to an antibody. The target-binding polypeptides, also called antibody-like molecules or antibody mimetics, generally have a molecular weight of 3-20 kDa, unlike antibodies, which have a molecular weight of about 150 kDa. Examples of the target-binding polypeptide include, but are not limited to, an affibody derived from Z-domain of protein A, an affilin derived from gamma-B crystallin or ubiquitin, affimer derived from systatin, an affitin derived from Sac7d of *Sulfolobus acidocaldarius*, an alphabody derived from triple helix coiled coil, an anticalin derived from lipocalin, an avimer derived from a cell membrane receptor domain, DARPin derived from an ankyrin repeat motif, Fynomer derived from the SH3 domain of Fyn, a Kunits domain peptide derived from the Kunits domain of protease inhibitor, a monobody derived from the $10^{th}$ type III domain of fibronectin, and nanoCLAMP derived from carbohydrate binding module 32-2 of NagH in *Clostridium perfringens*. Through various screening methods known in the art, such as phage display, ribosome display, etc., the target-binding polypeptide may be engineered to have binding affinity for any target antigen or hapten.

The terms "antibody", "antigen-binding fragment", and "target-binding polypeptide" used below are as defined above.

The term "cancer" as used herein is defined as disease characterized by the rapid and uncontrolled growth of aberrant cells. Cancer cells can spread locally or through the bloodstream and lymphatic system to other parts of the body. Examples of cancer include solid tumor and non-solid tumor (e.g., hematological tumor).

The term "tumor" as used herein, refers to an abnormal growth of tissue that may be benign, pre-cancerous, malignant, or metastatic.

Solid tumors are abnormal mass of tissue that usually does not contain cysts or liquid areas. Solid tumors can be benign or malignant. Different types of solid tumors are named, depending on types of cells that form tumors (such as sarcomas, carcinomas, and lymphomas). Examples of solid tumors, such as sarcomas and carcinoma, include fibrosarcoma, myxosarcoma, liposarcoma, chondrosarcoma, osteosarcoma and other sarcoma, synovioma, mesothelioma, Ewing's tumor, leiomyosarcoma, rhabdomyosarcoma, colon carcinoma, lymphoid malignancy, pancreatic cancer, breast cancer, lung cancer, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumor (such as glioma) (e.g., brainstem glioma and mixed gliomas), glioblastoma (also known as glioblastoma multiforme), astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma, and brain metastases.

Hematologic cancers are cancers of the blood or bone marrow. Examples of hematological (or hematogenous) cancers include leukemias, such as acute leukemias (e.g., acute lymphocytic leukemia, acute myelocytic leukemia, acute myelogenous leukemia and myeloblastic, promyelocytic, myelomonocytic, monocytic and erythroleukemia), chronic leukemias (e.g., chronic myelocytic (granulocytic) leukemia, chronic myelogenous leukemia, and chronic lymphocytic leukemia), etc., polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia, and myelodysplasia.

The term "autoimmune disease" as used herein, refers to a disorder that results from an autoimmune response. An autoimmune disease is the result of an inappropriate and excessive response to a self-antigen. Examples of autoimmune diseases include, but are not limited to, Addison's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, and ulcerative colitis.

As used herein, the term "cytotoxic" or "cytotoxicity" refers to killing or damaging cells. In one embodiment, cytotoxicity of activated cells against target cells means, for example, increased cytolytic activity of T lymphocytes.

In the present invention, (a) the targeting moiety and (b) the polypeptide binding to a chimeric antigen receptor, which are both responsible for the configuration of the switch molecule, are linked to each other via a covalent bond. By way of example, two or more polypeptide chains may be covalently linked by being expressed into a recombinant fused protein or may be connected by chemical conjugation into a conjugate.

According to another embodiment of the present invention, (a) the targeting moiety and (b) the polypeptide binding to a chimeric antigen receptor in the switch molecule may be linked to each other directly or indirectly via a linker (e.g., amino acid linker).

A person skilled in the art could conceive that a linker may be used between functional moieties to be usually fused in the production of a fusion protein and would understand that there are different kinds of linkers having different characteristics, for example, a flexible amino acid linker, a non-flexible linker, and a cleavable amino acid linker. The linkers have been used for the purpose of increasing expression levels, improving biological activity, and enabling targeting, or modifying pharmacokinetics of the fusion protein, or in order to increase stability and improve folding property of the fusion protein.

Therefore, according to a specific embodiment of the present invention, the complex may further contain at least one linker, for example, at least one linker selected from flexible amino acid linkers, non-flexible linkers, and cleavable amino acid linkers. According to a most specific embodiment of the present invention, the linker is arranged between (a) the targeting moiety and (b) the polypeptide binding to a chimeric antigen receptor.

According to an exemplary embodiment of the present invention, (a) the targeting moiety and (b) the polypeptide binding to a chimeric antigen receptor in the switch molecule are linked to each other via at least one linker.

In this regard, the linker may include an amino acid sequence represented by general formula $(G_nS_m)_p$ or $(S_mG_n)_p$, wherein n, m, and p each independently satisfying the following conditions:

n is an integer of 1 to 7;
m is an integer of 0 to 7;
with a proviso that a sum of n and m is an integer of 8 or less; and
p is an integer of 1 to 7.

In the linker according to a specific embodiment of the present invention, n=1 to 5 and m=0 to 5. In the linker according to a more specific embodiment of the present invention, n=4 and m=1. According to a further more specific embodiment of the present invention, the linker $(G_4S)_3$ or $(S_4G)_3$. According to another embodiment of the present invention, the linker is GGGGS.

According to a further embodiment of the present invention, the linker is VDGS. According to yet another specific embodiment of the present invention, the linker is ASGS.

Here, polypeptides or fusion proteins expressed in this disclosure, including the switch molecule, may contain at least one additional amino acid at the C-terminus and/or N-terminus thereof. The additional amino acid residue may be individually or collectively added for the purpose of improving, for example, productivity, purification, in vivo or in vitro stabilization, coupling with the complex, or detection. By way of example, a cysteine residue may be added to the C-terminus and/or N-terminus of the complex. The additional amino acid residue may provide a "tag" for purification or polypeptide detection and, for example, for interaction with an antibody specific therefor. In this regard, $His_6$ tag, $(HisGlu)_3$ tag ("HEHEHE" tag), "myc" (c-myc) tag, or "FLAG" tag may be provided for immobilized metal affinity chromatography (IMAC).

According to another aspect thereof, the present invention provides a nucleic acid comprising a nucleotide sequence coding for the switch molecule.

In an embodiment of the present invention, it would be obvious to a person skilled in the art that so long as it encodes the switch molecule, any nucleotide sequence may be used, without limitations thereto. The reason is that even if the nucleotide sequence undergoes mutation, the expression of the mutated nucleotide sequence into a protein may not cause a change in the protein sequence. This is called the degeneracy of codons. Therefore, the nucleotide sequence includes nucleotide sequences containing functionally equivalent codons, codons encoding the same amino acids (e.g., due to the degeneracy of codons, the number of codons for arginine or serine being six), or codons containing biologically equivalent amino acids.

As used herein, the term "nucleic acid" is intended to comprehensively encompass DNA (gDNA and cDNA) and RNA molecules, and nucleotides as basic constituent units in the nucleic acid molecules include naturally occurring nucleotides, and analogues with modified sugars or bases (Scheit, Nucleotide Analogs, John Wiley, New York (1980); and Uhlman & Peyman, Chemical Reviews, 90:543-584 (1990)).

Considering the above-described mutation having biologically equivalent activity, it should be construed that the nucleic acid molecules of the present invention encoding the amino acid sequences responsible for the constitution of the switch molecule also include sequences showing substantial identity therewith. The substantial identity refers to a sequence showing at least 60%, more preferably at least 70%, still more preferably at least 80%, still more preferably at least 90% nucleotide, and most specifically at least 95% identity when the sequence of the present invention and any other sequence are correspondingly aligned as much as possible and the aligned sequence is analyzed using algorithms commonly used in the art. Methods of alignment for sequence comparison are known in the art. Various methods and algorithms for alignment are disclosed in Smith and Waterman, Adv. Appl. Math. 2:482(1981); Needleman and Wunsch, J. Mol. Bio. 48:443(1970); Pearson and Lipman, Methods in Mol. Biol. 24: 307-31(1988); Higgins and Sharp, Gene 73:237-44(1988); Higgins and Sharp, CABIOS 5:151-3(1989); Corpet et al., Nuc. Acids Res. 16:10881-90 (1988); Huang et al., Comp. Appl. BioSci. 8:155-65(1992) and Pearson et al., Meth. Mol. Biol. 24:307-31, but are not limited thereto.

According to a further aspect thereof, the present invention provides a recombinant vector carrying a nucleic acid coding for the switch molecule.

The term "vector", as used herein, refers to a means for expressing a gene of interest in a host cell. Examples of the vector available herein include plasmid vectors; cosmid vectors; and viral vectors such as bacteriophage vectors, adenovirus vectors, retrovirus vectors, and adeno-associated virus vectors.

According to an exemplary embodiment of the present invention, the nucleic acid molecule encoding the switch molecule is operatively linked to a promoter in the vector.

As used herein, the term "operatively linked" refers to a functional linkage between a nucleic acid expression control sequence (e.g., a promoter, a signal sequence, or an array of transcription regulation factor binding sites) and another nucleic acid sequence, whereby the control sequence controls the transcription and/or translation of the nucleic acid sequence.

The vector system of the present invention can be constructed by various methods known in the art, and specific methods thereof are disclosed in Sambrook, et al., *Molecular Cloning, A Laboratory Manual*, Cold Spring Harbor Laboratory Press (2001), the teachings of which are incorporated herein by reference.

The vector of the present invention may be typically constructed as a vector for cloning or a vector for expression. In addition, the vector of the present invention may be constructed by using prokaryotic or eukaryotic cells as a host.

When the vector of the present invention is an expression vector, with an eukaryotic cell serving as a host cell, promoters derived from genomes of mammalian cells (e.g., metallothionein promoter, β-actin promoter, human hemoglobin promoter, and human muscle creatinine promoter) or promoters derived from mammalian viruses (e.g., adenovirus late promoter, vaccinia virus, 7.5K promoter, SV40 promoter, cytomegalovirus (CMV) promoter, HSV tk promoter, mouse mammary tumor virus (MMTV) promoter, HIV LTR promoter, moloney virus promoter, Epstein Barr Virus promoter, Rous Sarcoma Virus promoter) may be available. Generally, the vectors includes a polyadenylate sequence as a transcriptional termination sequence.

The vector of the present invention may be fused to another sequence to facilitate the purification of a polypeptide expressed therefrom. Examples of the sequence to be used for the fusion include, for example, glutathione S-transferase (Pharmacia, USA), maltose binding protein (NEB, USA), FLAG (IBI, USA), and 6× His (hexahistidine; Quiagen, USA).

The vector of the present invention includes, as a selective marker, an antibiotic-resistant gene that is ordinarily used in the art, and may include resistant genes against ampicillin, gentamycin, carbenicillin, chloramphenicol, streptomycin, kanamycin, geneticin, neomycin, and tetracycline.

According to another aspect thereof, the present invention provides a host cell transformed with the recombinant vector.

So long as it is known in the art to stabilize the vector of the present invention and continually clone and express the vector, any host cell may be employed in the present invention. Examples of the eukaryotic host cells suitable for the vector include monkey kidney cells 7(COS7), NSO cells, SP2/0, Chinese hamster ovary (CHO) cells, W138, baby hamster kidney (BHK) cells, MDCK, myeloma cell lines, HuT 78 cells, and HEK-293 cells, but are not limited thereto.

As used herein, the term "transformed", "transduced", or "transformed" refers to pertaining to a process for delivering or introducing an exogenous nucleic acid into a host cell. A "transformed", "transduced", or "transfected" cell is one which has been transformed, transduced, or transfected with an exogenous nucleic acid. The cell includes the primary subject cell and its progenies resulting from passages.

In accordance with a further aspect thereof, the present invention provides a composition comprising the switch molecule.

According to an embodiment of the present invention, the composition is an immunotherapeutic pharmaceutical composition comprising the switch molecule and a pharmaceutically acceptable carrier.

The term "immunotherapy", as used herein, refers to the artificial stimulation of the immune system to treat cancer. Immunotherapy can be either active or passive. Active immunotherapy includes i) cancer vaccine therapy in which cancer cells or a material produced from cancer cells are injected to the human body to boost the immune system, and ii) immune-modulating therapy in which immune-modulating agents such as cytokines (interferon, interleukin, etc.), growth factors, and so on are administered to activate specific leukocytes. Within passive immunotherapy includes the administration of therapeutic antibodies binding to specific cancer cells, and immune cell therapy. Examples of immune cell therapy include dendritic cell vaccine therapy, CAR-T (chimeric antigen receptor T cell therapy, natural killer (NK) cell therapy, cytotoxic T lymphocyte (CTL) therapy, and, adoptive cell transfer, but are not limited thereto. Herein, immune therapy refers mainly to the immune cell therapy.

Containing the switching molecule that comprises a targeting moiety binding to a cell surface molecule of a target cell, the pharmaceutical composition allow the target moiety to be engineered to have high binding affinity for any target antigens and as such, finds advantageous applications to the prophylaxis and therapy of various diseases.

The target antigen to which the targeting moiety binds may be selected from the group consisting of 4-1BB, 5T4, adenocarcinoma antigen, alpha-fetoprotein, BAFF, B lymphoma cells, C242 antigen, CA-125, carbonate dehydratase 9 (CA-IX), C-MET, CCR4, CD152, CD19, CD20, CD200, CD22, CD221, CD23 (IgE receptor), CD28, CD30 (TNFRSF8), CD33, CD4, CD40, CD44 v6, CD51, CD52, CD56, CD74, CD80, CEA, CNT0888, CTLA-4, DRS, EGFR, EpCAM, CD3, FAP, fibronectin extra domain-B, folate receptor 1, GD2, GD3 ganglioside, glycoprotein 75, GPNMB, HER2/neu, HGF, human scatter factor receptor kinase, IGF-1 receptor, IGF-I, IgG1, LI-CAM, IL-13, IL-6, insulin-like growth factor I receptor, integrin α5β1, integrin αvβ3, MORAb-009, MS4A1, MUC1, mucin CanAg, N-glycolylneuraminic acid, NPC-1C, PDGF-Ra, PDL192, phosphatidyl serine, prostate carcinoma cells, RANKL, RON, ROR1, SCH900105, SDC1, SLAMF7, TAG-72, tenascin C, TGF beta 2, TGF-beta, TRAIL-R1, TRAIL-R2, tumor antigen CTAA16.88, VEGF-A, VEGFR-1, VEGFR2, and vimentin, but is not limited thereto.

When the target antigen to which the targeting moiety binds specifically is CD19, the disease that the pharmaceutical composition of the present invention can treat includes human and mammalian diseases associated with CD19-expressing cells. In detail, the disease may be B cell malignancy including chronic lymphocytic leukemia (CLL), acute lymphocytic leukemia (ALL), pro-lymphocytic leukemia, hairy cell leukemia, common acute lymphocytic leukemia (CALLA), null-acute lymphoblastic leukemia, non-Hodgkin lymphoma, diffuse large B cell lymphoma (DLBCL), multiple myeloma, follicular lymphoma, splenic lymphoma, marginal zone lymphoma, mantle cell lymphoma, indolent B cell lymphoma, and Hodgkin lymphoma. In addition, the disease includes autoimmune disease and inflammatory disease associated with inadequate or enhanced B cell counts and/or activation. Examples of the autoimmune diseases and inflammatory diseases include multiple sclerosis, rheumatoid arthritis, and systemic lupus erythematosus (SLE).

So long as it is typically used for formulation, any pharmaceutically acceptable carrier may be contained in the pharmaceutical composition of the present invention. Examples of the pharmaceutically acceptable carrier include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil, but are not limited thereto.

The pharmaceutical composition of the present invention may further comprise a lubricant, a wetting agent, a sweetener, a flavorant, an emulsifier, a suspending agent, a preservative, and the like in addition to the above ingredients. With regard to suitable pharmaceutically acceptable carriers and preparations, reference may be made to Remington's Pharmaceutical Sciences (19$^{th}$ ed., 1995).

The pharmaceutical composition of the present invention may be administered orally or parenterally, for example, intravenously, subcutaneously, intramuscularly, intraperitoneally, intrasternally, intratumorally, topically, intranasally, intrapulmonarily, and rectally, but without limitations thereto.

Appropriate doses of the pharmaceutical composition of the present invention vary depending on various factors including a formulating method, a manner of administration, patient's age, body weight, sex, and morbidity, food, a time of administration, a route of administration, an excretion rate, and response sensitivity. An ordinarily skilled practitioner can easily determine and prescribe an effective dose for desired treatment or prevention. According to a preferable embodiment of the present invention, the daily dose of the pharmaceutical composition of the present invention is 0.0001-100 mg/kg. As used herein, the term "pharmaceutically effective amount" refers to an amount sufficient to prevent or treat the above-described diseases.

As used herein, the term "prevention" refers to a prophylactic or protective treatment of a disease or a disease condition. As used herein, the term "treatment" refers to a reduction, suppression, amelioration, or eradication of a disease condition.

The pharmaceutical composition of the present invention may be formulated into a unit dosage form or may be prepared in a multi-dose container by using a pharmaceutically acceptable carrier and/or excipient according to a method that can be easily implemented by a person having an ordinary skill in the art to which the present invention belongs. Here, the formulation may be in the form of a solution in an oily or aqueous medium, a suspension, an emulsion, an extract, a pulvis, a suppository, a powder, granules, a tablet, or a capsule, and may further contain a dispersant or a stabilizer.

The pharmaceutical composition of the present disclosure may further comprise other pharmaceutically active agents or drugs, for example, chemotherapeutic agents such as asparaginase, busulfane, carboplatin, cisplatin, daunorubicin, doxorubicin, fluorouracil, gemcitabine, hydroxyurea, methotrexate, paclitaxel, rituximab, vinblastine, vincristine, and the like.

According to a further aspect thereof, the present invention provides a complex comprising:
(a) a switch molecule for activating a chimeric antigen receptor-effector cell, the switch molecule comprising:
(aa) a targeting moiety binding to a cell surface molecule on a target cell; and
(bb) a polypeptide binding to a chimeric antigen receptor on the effect cell; and
(b) a polypeptide or fusion protein specifically binding to (targeting) the switch molecule.

According to an embodiment of the present invention, (aa) the targeting moiety and (bb) the polypeptide binding to a chimeric antigen receptor on the effector cell are each an antibody, an antigen-binding fragment of an antibody, or a target-binding polypeptide such as an affibody, and (b) the polypeptide or the fusion protein is also an antibody, an antigen-binding fragment of an antibody, a target-binding polypeptide such as an affibody, which all target the switch molecule, or is a chimeric antigen receptor including the same.

According to still another aspect thereof, the present invention provides a chimeric antigen receptor (CAR) comprising: (a) an extracellular domain including a target-binding polypeptide, such as an antibody, an antigen-binding fragment of an antibody, or an affibody, which targets the switch molecule; (b) a transmembrane domain; and an intracellular signaling domain.

According to a further still aspect thereof, the present invention provides a CAR-effector cell therapeutic system comprising (a) the switch molecule of the present invention and (b) the chimeric antigen receptor targeting the switch molecule.

When used, the CAR-effector cell therapeutic system can treat cancer (e.g., associated with CD19 expression-associated cell cancer) by administering to a patient in need thereof the switch molecule binding specifically to a surface antigen (e.g., CD19) on a specific cancer cell and (b) an effector cell (e.g., T cell, dendritic cell, etc.) expressing a chimeric antigen receptor targeting the switch molecule.

The term "chimeric antigen receptor" (CAR), as used herein, refers to an artificially constructed hybrid protein (fusion protein) or polypeptide containing a target binding domain (e.g., single-chain variable fragment (scFv)) linked to an effector cell signaling domain or an effector cell activating domain (e.g., T-cell signaling or T-cell activating domain). Chimeric antigen receptors have the ability to redirect T-cell specificity and reactivity toward a selected target in a non-MHC-restricted manner, exploiting the antigen-binding properties of monoclonal antibodies. The non-MHC-restricted antigen recognition gives T-cells expressing CARs the ability to recognize an antigen independent of antigen processing, thus bypassing a major mechanism of tumor escape. Moreover, when expressed in T-cells, CARs advantageously do not dimer with endogenous T-cell receptor (TCR) alpha and beta chain.

The chimeric antigen receptor of the present invention is a switchable chimeric antigen receptor (sCAR). An extracellular domain in a typical classical chimeric antigen receptor contains an antibody or antigen-binding fragment targeting a specific antigen (e.g., a tumor associated antigen (TAA) such as a HER2 antigen, a CD19 antigen, etc.). However, the extracellular domain in the chimeric antigen receptor of the present invention comprises an antibody, an antigen-binding fragment of an antibody, or a target-binding polypeptide. In addition, the antibody, the antigen-binding fragment of the antibody, or the target-binding polypeptide, which are all contained in the extracellular domain, does not target a cell surface antigen on a target cell, but the switch molecule (in detail, the CAR binding polypeptide in the switch molecule).

According to an embodiment of the present invention, the chimeric antigen receptor comprises Zb1 ($1^{st}$ sequence, $2^{nd}$ sequence), or Zb2 ($3^{rd}$ sequence, $4^{th}$ sequence) recognizing Zb1 and as such, can target the CAR-binding polypeptide of the switch molecule.

In an embodiment of the present invention, the intracellular signaling domain, which is an intracellular signaling domain in a stimulatory or costimulatory molecule, is responsible for activation of the CAR-expressing cells.

Non-limiting examples of the intracellular signaling domain include TCR, CD3 zeta, CD3 gamma, CD3 delta, CD3 epsilon, CD86, typical FcR gamma, FcR beta (Fc epsilon R1b), CD79a, CD79b, Fc gamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that binds specifically to CD83, CDS, ICAM-1, GITR, BAFFR, HVEM(LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96, CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other costimulatory molecules described herein, any derivative, variant, or fragment thereof, any synthetic sequence of a co-stimulatory molecule that has the same functional capability, and any combination thereof.

According to an embodiment thereof, (bb) the transmembrane domain comprises a transmembrane domain of a protein selected from the group consisting of the alpha, beta, or zeta chain of a T-cell receptor, CD27, CD28, CD3, epsilon, CD45, CD4, CD5, CD8(CD8α), CD9, CD16, CD22, CD33, CD37, CD64, CD80, CD86, CD134, CD137, and CD154.

According to an embodiment of the present invention, (cc) the intracellular signaling domain is a domain derived from the CD3ζ (CD3 zeta) chain.

According to another specific embodiment of the present invention, (cc) the intracellular signaling domain may further comprise a costimulatory molecule selected from the group consisting of OX40 (CD134), CD2, CD27, CD28, CDS, ICAM-1, LFA-1(CD11a/CD18), and 4-1BB (CD137). The intracellular signaling domain may be obtained or derived from a singling molecule within other cells known in the art in addition to the aforementioned domain and may comprise the entirety or a fragment of the origin molecule thereof.

The transmembrane domain and intracellular signaling domain in the chimeric antigen receptor of the present invention may be included in one or more combinations of the transmembrane domains and intracellular signaling domains described above. For example, the chimeric antigen receptor of the present invention may comprise the transmembrane domain of CD8α and the intracellular signaling domains of CD28 and CD3ζ.

As used herein, the term "switch molecule" refers to an adaptor molecule in a T cell therapy product using the chimeric antigen receptor, that is, called CAR-T cell therapy product, which separates the target recognition domain and intracellular signaling domain of CAR from each other and mediates the same. Switch molecules allow CAR-expressing cells to be redirected to target heterogenous or resistant tumors or to be reduced in terms of activity by dosage thereof when side effects are generated due to excessive activation of the CAR-expressing cells (Cao et al., Angew Chem Int Ed Engl. 2016 Jun. 20; 55(26): 7520-7524).

According to yet another embodiment thereof, the present invention provides a chimeric antigen receptor-expressing effector cell wherein the chimeric antigen receptor targets (b) the chimeric antigen receptor-binding polypeptide (e.g., an affibody molecule) of the switch molecule.

According to a yet still another embodiment thereof, the present invention provides a CAR-effector cell therapeutic system comprising:

(a) the above-described switch molecule of the present invention, and (b) an effector cell expressing a chimeric antigen receptor targeting the above-described switch molecule of the present invention.

When used, the CAR-effector cell therapeutic system can treat cancer by administering to a patient in need thereof the switch molecule binding specifically to a surface antigen (e.g., CD19) on a specific cancer cell and (b) an effector cell (e.g., T cell, dendritic cell, etc.) expressing a chimeric antigen receptor targeting the switch molecule.

According to an embodiment of the present invention, the effector cell is selected from the group consisting of a dendritic cell, a killer dendritic cell, a mast cell, a natural killer cell, a B lymphocyte, a T lymphocyte, a macrophage, and a precursor cell thereof.

According to a specific embodiment of the present invention, the T lymphocyte may be selected from an inflammatory T lymphocyte, a cytotoxic T lymphocyte, a regulatory T lymphocyte, and a helper T lymphocyte.

According to a yet further aspect thereof, the present invention provides a method comprising a step of administering an effector cell expressing the chimeric antigen receptor and a switch molecule binding to the chimeric antigen receptor to a subject that needs to be treated.

In an embodiment of the present invention, the method is a method for treating a disease or condition associated with tumors or cancer.

In another embodiment of the present invention, the method is a method for treating a disease or condition associated with autoimmunity.

According to an embodiment of the present invention, the method for treating a disease or condition associated with tumors or cancer further comprises a step of additionally administering to the subject at least one switch molecule different from the previously administered switch molecule and binding to a cell surface molecule on the target cell.

When generated during a procedure for treating a disease or condition associated with a tumor or cancer with CAR-T, a mutation in a cell surface molecule on cancer cells hinders preexisting CARs from recognizing the mutated cancer cells, thus reducing therapeutic effects or making it impossible to treat the disease or condition. In this regard, if further administered to the subject, a novel switch molecule that targets a surface molecule on the mutated cells may exhibit a persistent therapeutic effect, in lieu of the previously admitted switch molecule.

The method for treating a disease or condition associated with tumors or cancer according to the present invention employs the effector cell expressing CAR and the switch molecule binding to CAR described above. Hence, the common descriptions of the overlapping ingredients are omitted in order to avoid undue redundancy leading to the complexity of this specification.

According to a yet still further aspect thereof, the present invention provide a method for restraining activity of an effector cell expressing the chimeric antigen receptor (CAR-effector cell) in a subject in need thereof, the method comprising the steps of: (a) administering to the subject the CAR-effector cell and the switch molecule binding to the chimeric antigen receptor; and (b) additionally administering to the subject either at least one switch molecule different from the previously administered switch molecule and binding to a cell surface molecule on the target cell or a targeting moiety-lacking polypeptide binding to the chimeric antigen receptor.

When generated in the course of treating a tumor- or cancer-associated disease or condition with CAR-T, the undue activation of CAR-T cells may cause a complication such as tumor lysis syndrome (TLS), cytokine release syndrome (CRS), etc., which are fetal to the patient. In the CAR-effector cell therapeutic system employing the switch molecule according to the present invention, the CAR-effector cell recognizes a cell surface molecule on cancer cells not directly, but indirectly via the switch molecule containing a polypeptide binding to CAR. Hence, when either one or more switch molecules different from the previously administered switch molecule and binding to a cell surface molecule on target cells or a targeting moiety-lacking polypeptide binding to the chimeric antigen receptor is additionally administered to a subject, CAR can no longer target cancer cells, thereby restraining undue activity of CAR-T cells.

Advantageous Effects

Features and advantageous of the present invention are summarized as follows:

The present invention provides a switch molecule for activating a chimeric antigen receptor-effector cell.

Also, the present invention provides (a) a switch molecule for activating a chimeric antigen receptor-effector cell, and (b) a polypeptide or fusion protein binding specifically to the switch molecule.

In addition, the present invention provides a chimeric antigen receptor (CAR) comprising the switch molecule or the fusion protein.

(i) When severe toxicity is generated during the use of the switch molecule of the present invention, a targeting moiety-lacking switch molecule is administered to control the activity of CAR-T cells and thus to enhance the safety of CAR-T cells, and (ii) in order to cope with mutation of an antigen or to treat various carcinomas, a switch molecule targeting a new antigen generated due to the mutation or a switch molecule targeting a different tumor-associated antigen (TAA) may be administered to a patient, whereby cancer can be effectively treated.

BRIEF DESCRIPTION OF THE DRAWINGS

FIG. 2a is view showing the binding of Zb1-Fc protein to a sensor chip having a switch molecule immobilized thereto and FIG. 2b is a view showing the binding of Zb2-Fc protein.

FIG. 5a is a view showing the binding of Zb2-Fc in the switch molecule to HER2 protein as measured by a BLI assay. FIGS. 5b and 5c are views showing that switch molecule and Zb2-Fc can selectively target HER2-positive cells only, as measured in the HER2-positive cell OE-19 (5b) and the HER2-negative cell MDA-MB-231 (5c).

FIG. 6 is a schematic view of various CD19-targeting switch molecules.

FIGS. 7a and 7b are views showing that a switch molecule comprising Zb1 or Zb2 can selectively target CD19-positive cancer cells, with the aid of Zb2-Fc or Zb1-Fc, as measured in the CD19-positive cell Raji (7a) and the CD19-negative cell Jurkat (7b).

FIG. 8a shows amounts of interferon gamma in the culture as assayed by ELISA and FIG. 8b shows cell viability in terms of cytotoxicity as measured by luminescence assay.

DETAILED DESCRIPTION

Figure 1:
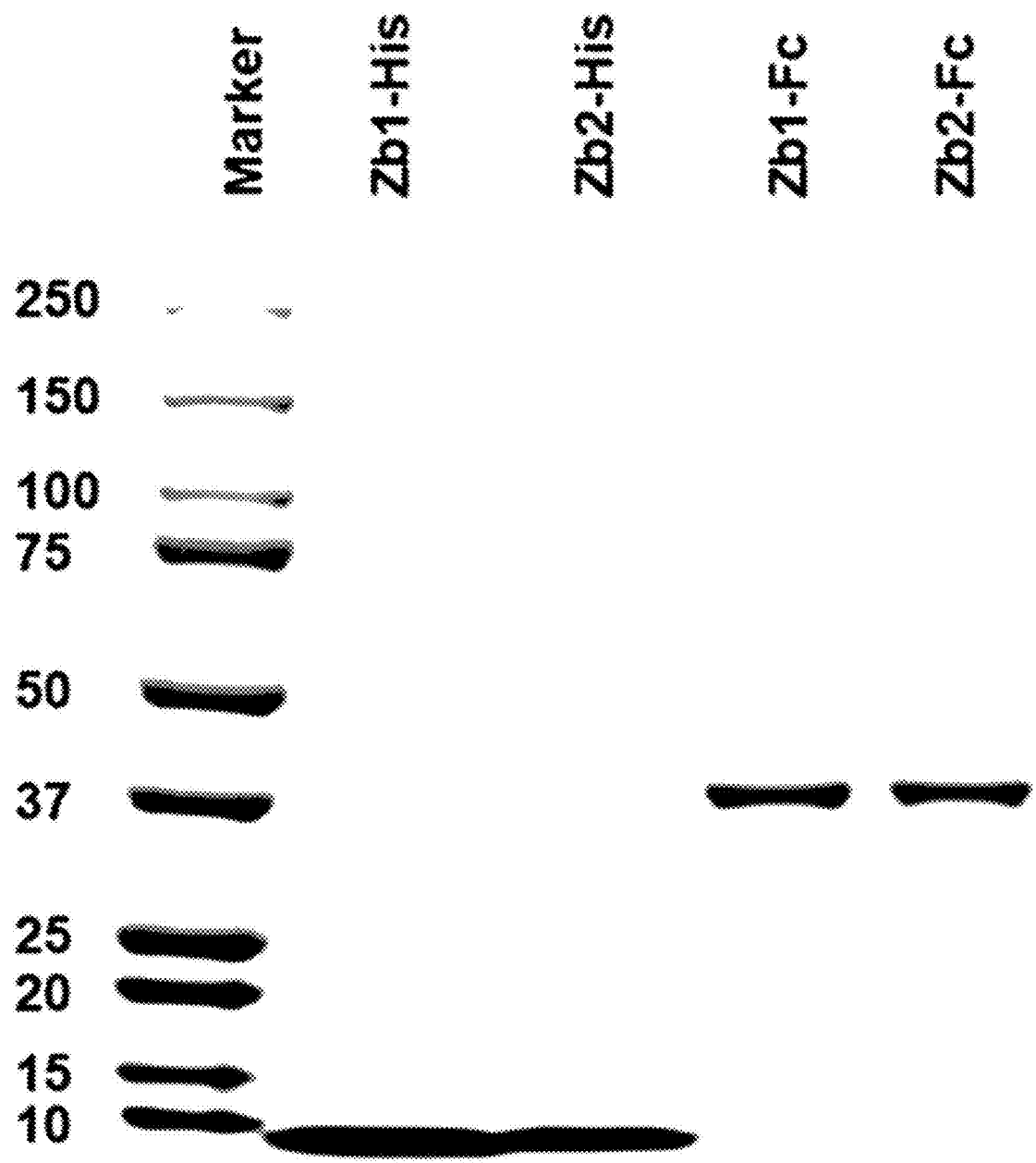
FIG. 1 is a view showing the production of His- or Fc-coupled affibodies (Zb) that bind specifically to each other, at predicted sizes, as analyzed by SDS-PAGE.

Hereinafter, the present invention will be described in detail with reference to examples. These examples are only for illustrating the present invention more specifically, and it will be apparent to those skilled in the art that the scope of the present invention is not limited by these examples.

EXAMPLES

Unless stated otherwise, "%", used to indicate concentrations of particular substances, stands for (wt./wt.) % for solid/solid, (wt./vol.) % for solid/liquid, and (vol./vol.) % for liquid/liquid throughout the specification.

Example 1: Assay for Specific Binding Between Antigen-Binding Site of Switchable CAR and Switch Molecule (Specific Binding between Affibodies)

The novel switchable chimeric antigen receptor (sCAR) system of the present invention employs an antigen-binding site of a CAR and an affibody (abbreviated to "Z body" or "Zb" herein) as a switch molecule binding to the antigen-binding site of the CAR.

In the following experiments, the present inventors examined whether use could be made of an antigen binding site of the CAR and an affibody pair as a switch molecule binding to the antigen binding site of the CAR.

Two kinds of affibodies (Zb1 and Zb2), which specifically bind to each other, were tagged with histidine (Zb1-His and Zb2-His) and grafted with an Fc region (Zb1-Fc, Zb2-Fc) with the aid of bacterial and animal cells, and the resulting proteins were examined for binding therebetween by Bio-Layer Interferometry (BLI) assay.

TABLE 1

| SEQ ID NO: | Name | Type | Sequence (5'→3') |
|---|---|---|---|
| 1 | Zb1-His | Nucleotide | GTCGATAACAAATTCAACAAAGAGCTGGGCTGG GCTACCTGGGAGATTTTTAATCTTCCGAATTTA AACGGTGTTCAAGTGAAAGCTTTTATCGATAGC CTGCGCGACGATCCTAGCCAGAGCGCAAATTTG CTGGCCGAAGCAAAAAAACTGAATGATGCGCAG GCGCCAAAGCTCGAGCACCACCACCACCACCAC |
| 2 | | Amino acid | VDNKFNKELGWATWEIFNLPNLNGVQVKAFIDS LRDDPSQSANLLAEAKKLNDAQAPKLEHHHHHH |

TABLE 1-continued

| SEQ ID NO: | Name | Type | Sequence (5'→3') |
|---|---|---|---|
| 3 | Zb2-His | Nucleotide | GTCGATAACAAATTCAACAAAGAGCGCGTAATT GCAATCGGTGAAATTATGCGTCTGCCAAACCTG AATAGCCTGCAGGTTGTGGCCTTTATAAACTCT CTGCGCGATGACCCGAGTCAGTCAGCAAACCTG CTTGCGGAAGCGAAAAAGCTGAATGATGCCCAA GCTCCTAAACTCGAGCACCACCACCACCACCAC |
| 4 | | Amino acid | VDNKFNKERVIAIGEIMRLPNLNSLQVVAFINS LRDDPSQSANLLAEAKKLNDAQAPKLEHHHHHH |
| 5 | Zb1-Fc | Nucleotide | GTCGATAACAAATTCAACAAAGAGCTGGGCTGG GCTACCTGGGAGATTTTTAATCTTCCGAATTTA AACGGTGTTCAAGTGAAAGCTTTTATCGATAGC CTGCGCGACGATCCTAGCCAGAGCGCAAATTTG CTGGCCGAAGCAAAAAAACTGAATGATGCGCAG GCGCCAAAGGGCCAGGCCGGCCAGGAGCCCAAA TCTAGCGACAAAACTCACACAAGCCCACCGTGC CCAGCACCTGAACTCCTGGGGGGACCGTCAGTC TTCCTCTTCCCCCCAAAACCCAAGGACACCCTC ATGATCTCCCGGACCCCTGAGGTCACATGCGTG GTGGTGGACGTGAGCCACGAAGACCCTGAGGTC AAGTTCAACTGGTACGTGGACGGCGTGGAGGTGCA TAATGCCAAGACAAAGCCGCGGGAGGAGCAGTA CAACAGCACGTACCGTGTGGTCAGCGTCCTCAC CGTCCTGCACCAGGACTGGCTGAATGGCAAGGA GTACAAGTGCAAGGTCTCCAACAAAGCCCTCCC AGCCCCCATCGAGAAAACCATCTCCAAAGCCAA AGGGCAGCCCCGAGAACCACAGGTGTACACCCT GCCCCCATCCCGGGATGAGCTGACCAAGAACCA GGTCAGCCTGACCTGCCTGGTCAAAGGCTTCTA TCCCAGCGACATCGCCGTGGAGTGGGAGAGCA ATGGGCAGCCGGAGAACAACTACAAGACCACGC CTCCCGTGCTGGACTCCGACGGCTCCTTCTTCC TCTACAGCAAGCTCACCGTGGACAAGAGCAGGT GGCAGCAGGGGAACGTCTTCTCATGCTCCGTGA TGCATGAGGCTCTGCACAACCACTACACGCAGA AGAGCCTCTCCCTGTCCCCGGGTAAA |
| 6 | | Amino acid | VDNKFNKELGWATWEIFNLPNLNGVQVKAFIDSL RDDPSQSANLLAEAKKLNDAQAPKGQAGQEPKSS DKTHTSPPCPAPELLGGPSVFLFPPKPKDTLMIS RTPEVTCVVVDVSHEDPEVKFNWYVDGVEVHNAK TKPREEQYNSTYRVVSVLTVLHQDWLNGKEYKCK VSNKALPAPIEKTISKAKGQPREPQVYTLPPSRD ELTKNQVSLTCLVKGFYPSDIAVEWESNGQPENN YKTTPPVLDSDGSFFLYSKLTVDKSRWQQGNVFS CSVMHEALHNHYTQKSLSLSPGK |
| 7 | Zb2-Fc | Nucleotide | GTCGATAACAAATTCAACAAAGAGCGCGTAATTG CAATCGGTGAAATTATGCGTCTGCCAAACCTGAA TAGCCTGCAGGTTGTGGCCTTTATAAACTCTCTG CGCGATGACCCGAGTCAGTCAGCAAACCTGCTT GCGGAAGCGAAAAAGCTGAATGATGCCCAAGCT CCTAAAGGCCAGGCCGGCCAGGAGCCCAAATCT AGCGACAAAACTCACACAAGCCCACCGTGCCCA GCACCTGAACTCCTGGGGGGACCGTCAGTCTTC CTCTTCCCCCCAAAACCCAAGGACACCCTCATG ATCTCCCGGACCCCTGAGGTCACATGCGTGGTG GTGGACGTGAGCCACGAAGACCCTGAGGTCAAG TTCAACTGGTACGTGGACGGCGTGGAGGTGCAT AATGCCAAGACAAAGCCGCGGGAGGAGCAGTAC AACAGCACGTACCGTGTGGTCAGCGTCCTCACC GTCCTGCACCAGGACTGGCTGAATGGCAAGGAG TACAAGTGCAAGGTCTCCAACAAAGCCCTCCCA GCCCCCATCGAGAAAACCATCTCCAAAGCCAAA GGGCAGCCCCGAGAACCACAGGTGTACACCCT GCCCCCATCCCGGGATGAGCTGACCAAGAACCA GGTCAGCCTGACCTGCCTGGTCAAAGGCTTCTA TCCCAGCGACATCGCCGTGGAGTGGGAGAGCA ATGGGCAGCCGGAGAACAACTACAAGACCACGC CTCCCGTGCTGGACTCCGACGGCTCCTTCTTCC TCTACAGCAAGCTCACCGTGGACAAGAGCAGGT GGCAGCAGGGGAACGTCTTCTCATGCTCCGTGA TGCATGAGGCTCTGCACAACCACTACACGCAGA AGAGCCTCTCCCTGTCCCCGGGTAAA |

TABLE 1-continued

| SEQ ID NO: | Name | Type | Sequence (5'→3') |
|---|---|---|---|
| 8 | | Amino acid | VDNKFNKERVIAIGEIMRLPNLNSLQWAFINSLRD DPSQSANLLAEAKKLNDAQAPKGQAGQEPKSSDKT HTSPPCPAPELLGGPSVFLFPPKPKDTLMISRTPE VTCVVVDVSHEDPEVKFNWYVDGVEVHNAKTKPRE EQYNSTYRWSVLTVLHQDWLNGKEYKCKVSNKAL PAPIEKTISKAKGQPREPQVYTLPPSRDELTKNQV SLTCLVKGFYPSDIAVEWESNGQPENNYKTTPPVL DSDGSFFLYSKLTVDKSRWQQGNVFSCSVMHEAL HNHYTQKSLSLSPGK |

Figure 2A:
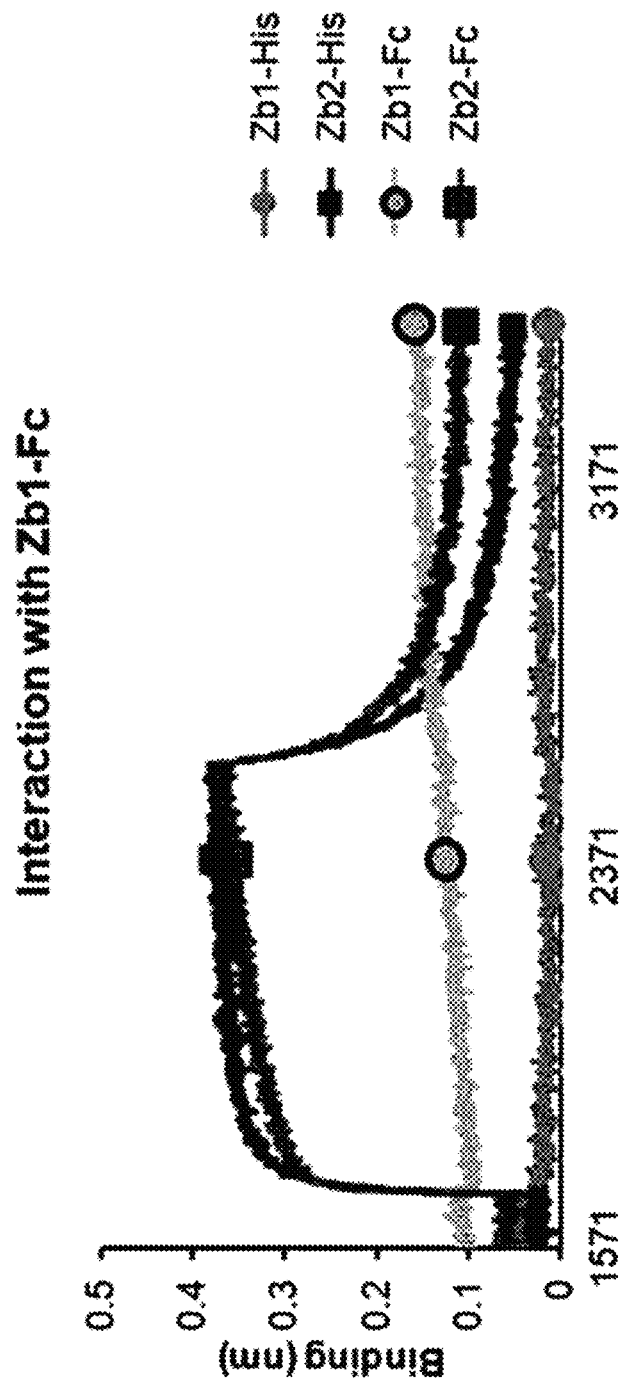
FIGS. 2A and 2B are views showing specific binding between Zb1 and Zb2 as measured by BLI assay.
Figure 2B:
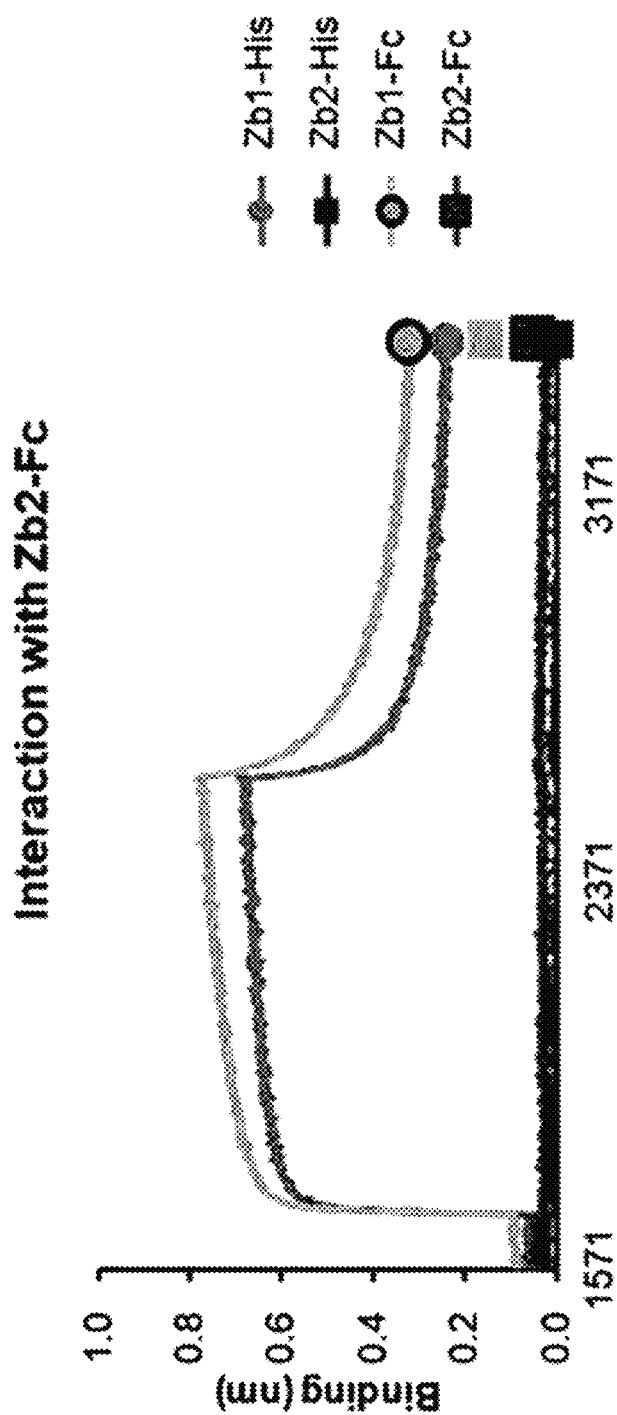

In brief, Zb1-His (SEQ ID NOS: 1 and 2) and Zb2-His (SEQ ID NOS: 3 and 4) genes were cloned into pET21a (Novagen, Cat No. 69740-3) by using the restriction enzymes NcoI and XhoI. The cloned vectors were transformed into BL21(DE3) competent cells (Novagen, Cat No. 69450) which were then cultured in the presence of 1 mM IPTG (LPS solution, Cat No. IPTG025) to express the proteins. From the cytoplasm of the culture cells, Zb-His protein was purified using Ni-NTA resin (Qiagen, Cat No. 30410). Zb1-Fc (SEQ ID NOS: 5 and 6) and Zb2-Fc (SEQ ID NOS: 7 and 8) genes were cloned into pCEP4 vector (Invitrogen, Cat. No. V044-50) by using the restriction enzyme SfiI. Subsequently, the cloned vector was transiently transfected into FreeStyle 293F (Invitrogen, Cat. No. R790-07) cells with the aid of polyethyleneimine (Polyscience Inc, Cat. No. 23966). From the cell culture, the proteins were purified using protein-A ceramic HyperD F resins (PALL, Cat. No. 20078-028). The purified proteins were quantitated using Protein assay dye (Bio-Rad, Cat. No. 500-0006) and then examined for size and purity through coomassie blue staining after SDS-PAGE (FIG. 1). As shown in FIG. 1, Zb-His and Zb-Fc proteins were expressed at the respective predicted sizes 7.3 kDa and 32.5 kDa thereof. In addition, specific binding between Zb1 and Zb2 was examined by BLI assay using Octet QKe instrument (PallForteBio, Cat. No. 30-5046). Zb1-His, Zb2-His, Zb1-Fc, and Zb2-Fc proteins were each immobilized at a concentration of 10 mg/mL to AR2G sensor chip (Fortebio, Cat. No. 18-5093) by an amine coupling approach using EDC/NHS. The Zb-immobilized sensor chip was coupled with Zb1-Fc or Zb2-Fc at a concentration of 10 mg/mL for 15 min (FIGS. 2a and 2b). As can be seen in FIGS. 2a and 2b, Zb1-Fc was found to bind Zb2-His and Zb2-Fc while Zb2-Fc was found to bind Zb1-His and Zb1-Fc. Thus, the affibodies (e.g., Zb1 and Zb2) that bind specifically to each other to form a pair can be used as an antigen-binding side of a CAR and a switch molecule binding to the antigen-binding site of CAR.

Example 2: Construction of HER2 Targeting Switch Molecule Using Affibody (Zb)

The switchable CAR system of the present invention utilizes a switch molecule including an affibody (Zb) targeting a specific cancer cell, and a CAR including an affibody specifically binding to the switch molecule.

Three kinds of HER2-targeting switch molecules including affibody (e.g., Zb1) were prepared and examined for binding between switch molecules and affibody molecules (antigen-binding site of CAR) and the switch molecule-affibody complexes (switch molecules and CAR) were evaluated for targeting performance.

Example 2-1: Construction of Three Kinds of HER2-Targeting Switch Molecules

The switch molecules zHER2-Zb1, scHER2-Zb1, and igHER2-Zb1 in which HER2-targeting affibody (zHER2), HER2-targeting scFv of trastuzumab (scHER2), and IgG-type antibody (igHER2) are conjugated with Zb1, respectively, were each cloned and produced.

TABLE 2

| SEQ ID NO: | Name | Type | Sequence (5'→3') |
|---|---|---|---|
| 9 | zHER2-(S4G)3-Zb1 | Nucleotide | GTTGACAACAAGTTTAACAAGGAAATGCGTAAC GCGTACTGGGAAATTGCCCTGCTGCCAAATCT GAATAACCAGCAGAAACGTGCTTTCATCCGCA GCCTGTATGACGATCCTAGCCAGAGCGCCAAT CTGCTTGCTGAGGCAAAAAAATTGAATGATGCG CAAGCACCGAAATcatcaagcagtggaagttctt catccggctcatcatcttcaggtgtcgataacaa attcaacaaagagctgggctgggctacctgggag attttaatcttccgaatttaaacggtgttcaag tgaaagcttttatcgatagcctgcgcgacgatcc tagccagagcgcaaatttgctggccgaagcaaaa aaactgaatgatgcgcaggcgccaaag |
| 10 | | Amino acid | VDNKFNKEMRNAYWEIALLPNLNNQQKRAFIRSL YDDPSQSANLLAEAKKLNDAQAPKSSSGSSSS GSSSSGVDNKFNKELGWATWEIFNLPNLNGVQV KAFIDSLRDDPSQSANLLAEAKKLNDAQAPK |

TABLE 2-continued

| SEQ ID NO: | Name | Type | Sequence (5'→3') |
|---|---|---|---|
| 11 | SCHER2-(S4G)3-Zb1 | Nucleotide | GACATTCAGATGACGCAGTCACCATCGTCGTT GTCAGCGTCGGTAGGTGATCGCGTCACGATTA CCTGTCGTGCATCCCAAGATGTGAACACTGCA GTAGCGTGGTACCAGCAGAAACCGGGGAAAG CTCCGAAACTTCTGATTTACTCGGCGAGTTTCC TGTATAGTGGCGTTCCAAGTCGCTTTAGCGGTT CCCGTTCTGGCACGGATTTCACACTGACCATCT CAAGCTTGCAGCCGGAAGATTTTGCCACCTATT ACTGCCAACAGCACTATACCACTCCTCCGACCT TTGGCCAAGGCACCAAAGTGGAGATCAAACGC GGCGGAGGTGGTAGTGGTGGCGGTGGGTCTG GCGGCGGTGGGAGCGAAGTGCAGCTGGTCGA ATCGGGTGGCGGATTAGTGCAGCCTGGAGGCT CCTTACGCCTGAGCTGTGCAGCGAGCGGCTTC AACATCAAGGACACCTACATACATTGGGTTCGC CAAGCTCCGGGCAAAGGTCTGGAGTGGGTTGC TCGTATCTATCCCACTAATGGGTATACACGCTA TGCCGATAGCGTGAAAGGCCGGTTTACCATTA GCGCCGATACGAGCAAGAATACGGCGTATCTG CAGATGAACTCTCTGCGTGCCGAAGATACAGC GGTCTACTACTGCTCTCGTTGGGGTGGTGACG GGTTTTATGCAATGGACTATTGGGGCCAAGGA ACCCTCGTGACGGTTTCCTCATcatcaagcag tggaagttcttcatccggctcatcatcttcag gtgtcgataacaaattcaacaaagagctgggc tgggctacctgggagattttttaatcttccgaa tttaaacggtgttcaagtgaaagctttatcg atagcctgcgcgacgatcctagccagagcgca aatttgctggcgaagcaaaaaaaactgaatga tgcgcaggcgccaaag |
| 12 | | Amino acid | DIQMTQSPSSLSASVGDRVTITCRASQDVNTAV AWYQQKPGKAPKLLIYSASFLYSGVPSRFSGSR SGTDFTLTISSLQPEDFATYYCQQHYTTPPTFG QGTKVEIKRGGGGSGGGGSGGGGSEVQLVESGG GLVQPGGSLRLSCAASGFNIKDTYIHWVRQAPG KGLEWVARIYPTNGYTRYADSVKGRFTISADTS KNTAYLQMNSLRAEDTAVYYCSRWGGDGFYAMD YWGQGTLVTVSSSSSGSSSSGSSSSGVDNKFN KELGWATWEIFNLPNLNGVQVKAFIDSLRDDPS QSANLLAEAKKLNDAQAPK |
| 13 | igHER2-(S4G)3-Zb1 heavy chain | Nucleotide | GAGGTGCAGCTGGTGGAATCTGGCGGAGGAC TGGTGCAGCCTGGCGGCTCTCTGAGACTGTCT TGTGCCGCCTCCGGCTTCAACATCAAGGACAC CTACATCCACTGGGTCCGACAGGCCCCTGGCA AGGGACTGGAATGGGTGGCCCGGATCTACCC CACCAACGGCTACACCAGATACGCCGACTCCG TGAAGGGCCGGTTCACCATCTCCGCCGACACC TCCAAGAACACCGCCTACCTGCAGATGAACTC CCTGAGAGCCGAGGACACCGCCGTGTACTACT GCTCCAGATGGGGAGGCGACGGCTTCTACGCT ATGGACTATTGGGGCCAGGGCACCCTGGTCAC CGTGTCCTCTGCTTCTACCAAGGGCCCCTCCG TGTTCCCTCTGGCCCCTTCCAGCAAGTCCACC TCTGGCGGAACCGCTGCTCTGGGCTGCCTGGT CAAGGACTACTTCCCCGAGCCTGTGACCGTGT CCTGGAACTCTGGCGCTCTGACCTCCGGCGTG CACACCTTTCCAGCCGTGCTGCAGTCCTCCGG CCTGTACTCTCTGTCCTCCGTCGTGACCGTGC CTTCCAGCTCTCTGGGCACCCAGACCTACATC TGCAACGTGAACCACAAGCCCTCCAACACCAA GGTGGACAAGAAGGTGGAACCCAAGTCCTGCG ACAAGACCCACACCTGTCCCCCTTGTCCTGCC CCTGAACTGCTGGGCGGACCTTCCGTGTTCCT GTTCCCCCCAAAGCCCAAGGACACCCTGATGA TCTCCCGGACCCCCGAAGTGACCTGCGTGGTG GTGGATGTGTCCCACGAGGACCCTGAAGTGAA GTTCAATTGGTACGTGGACGGCGTGGAAGTGC ACAACGCCAAGACCAAGCCCAGAGAGGAACAG TACAACTCCACCTACCGGGTGGTGTCCGTGCT GACCGTGCTGCACCAGGACTGGCTGAACGGC AAAGAGTACAAGTGCAAGGTGTCCAACAAGGC CCTGCCTGCCCCCATCGAAAAGACCATCTCCA AGGCCAAGGGCCAGCCCCGCGAGCCTCAGGT GTACACACTGCCCCCCAGCCGGGAAGAGATGA |

TABLE 2-continued

| SEQ ID NO: | Name | Type | Sequence (5'→3') |
|---|---|---|---|
| | | | CCAAGAACCAGGTGTCCCTGACCTGTCTGGTC AAGGGCTTCTACCCCTCCGACATTGCCGTGGA ATGGGAGTCCAACGGCCAGCCCGAGAACAACT ACAAGACCACCCCCCCTGTGCTGGACTCCGAC GGCTCATTCTTCCTGTACTCCAAGCTGACCGTG GACAAGTCCCGGTGGCAGCAGGGCAACGTGTT CTCCTGCTCTGTGATGCACGAGGCCCTGCACA ACCACTACACCCAGAAGTCCCTGTCCCTGAGC CCCGGCAAGTcatcaagcagtggaagttcttc atccggctcatcatcttcaggtgtcgataaca aattcaacaaagagctgggctgggct acctgggagattttaatcttccgaatttaaac ggtgttcaagtgaaagcttttatcgatagcctg cgcgacgatcctagccagagcgcaaatttgctg gccgaagcaaaaaaactgaatgatgcgcaggcg ccaaag |
| 14 | | Amino acid | EVQLVESGGGLVQPGGSLRLSCAASGFNIKDTY IHWVRQAPGKGLEWVARIYPTNGYTRYADSVKG RFTISADTSKNTAYLQMNSLRAEDTAVYYCSRW GGDGFYAMDYWGQGTLVTVSSASTKGPSVFPLA PSSKSTSGGTAALGCLVKDYFPEPVTVSWNSGA LTSGVHTFPAVLQSSGLYSLSSVVTVPSSSLGT QTYICNVNHKPSNTKVDKKVEPKSCDKTHTCPP CPAPELLGGPSVFLFPPKPKDTLMISRTPEVTC VVVDVSHEDPEVKFNWYVDGVEVHNAKTKPREE QYNSTYRVVSVLTVLHQDWLNGKEYKCKVSNKA LPAPIEKTISKAKGQPREPQVYTLPPSREEMTK NQVSLTCLVKGFYPSDIAVEWESNGQPENNYKT TPPVLDSDGSFFLYSKLTVDKSRWQQGNVFSCS VMHEALHNHYTQKSLSLSPGKSSSSGSSSSGSS SSGVDNKFNKELGWATWEIFNLPNLNGVQVKAF IDSLRDDPSQSANLLAEAKKLNDAQAPK |
| 15 | igHER2- (S4G)3- Zb1 light chain | Nucleotide | GACATCCAGATGACCCAGTCCCCCTCCAGCCT GTCTGCCTCTGTGGGCGACAGAGTGACCATCA CCTGTCGGGCCTCCCAGGACGTGAACACCGC CGTGGCTTGGTATCAGCAGAAGCCCGGCAAGG CCCCCAAGCTGCTGATCTACTCCGCCTCCTTC CTGTACTCCGGCGTGCCCTCCAGATTCTCCGG CTCCAGATCTGGCACCGACTTCACCCTGACCA TCTCCAGCCTGCAGCCCGAGGACTTCGCCACC TACTACTGCCAGCAGCACTACACCACCCCCCC TACCTTTGGCCAGGGCACCAAGGTGGAAATCA AGCGGACCGTGGCCGCTCCCTCCGTGTTCATC TTCCCACCTTCCGACGAGCAGCTGAAGTCCGG CACCGCCTCTGTCGTGTGCCTGCTGAACAACT TCTACCCCCGCGAGGCCAAGGTGCAGTGGAA GGTGGACAATGCCCTGCAGTCCGGCAACTCCC AGGAATCCGTCACCGAGCAGGACTCCAAGGAC AGCACCTACTCCCTGTCCTCCACCCTGACCCT GTCCAAGGCCGACTACGAGAAGCACAAGGTGT ACGCCTGCGAAGTGACCCACCAGGGCCTGTCC AGCCCCGTGACCAAGTCCTTCAACCGGGGCGA GTGC |
| 16 | | Amino acid | DIQMTQSPSSLSASVGDRVTITCRASQDVNTAVA WYQQKPGKAPKLLIYSASFLYSGVPSRFSGSRSG TDFTLTISSLQPEDFATYYCQQHYTTPPTFGQGT KVEIKRTVAAPSVFIFPPSDEQLKSGTASVVCL LNNFYPREAKVQWKVDNALQSGNSQESVTEQDS KDSTYSLSSTLTLSKADYEKHKVYACEVTHQGL SSPVTKSFNRGEC |

Figure 3:
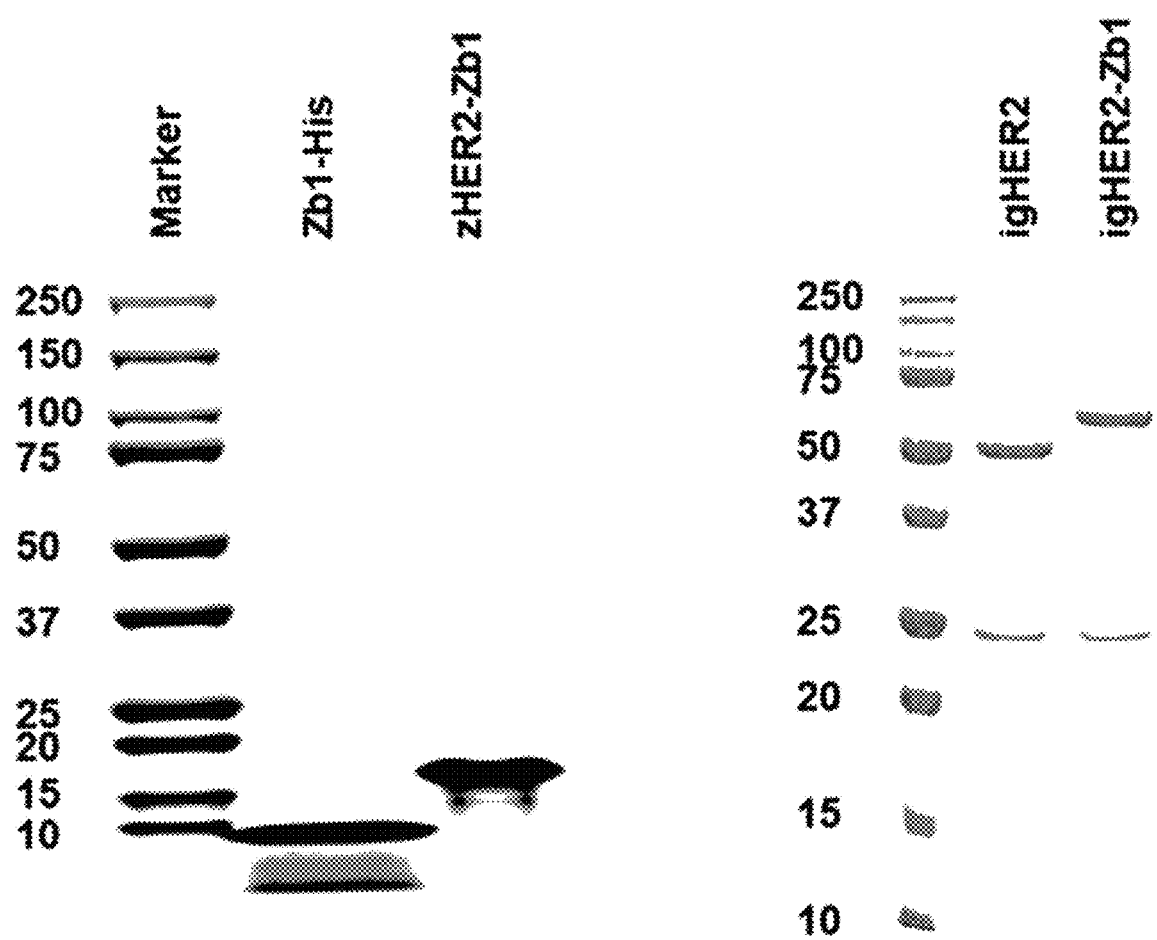
FIG. 3 is a view showing the production of switch molecules in which HER2-targeting affibody (zHER2) or IgG antibody (igHER2) is linked to Zb1, as analyzed by SDS-PAGE.

A HER2-targeting site was linked to Zb1 via a (G$_4$S)$_3$ linker. zHER2-Zb1 and scHER2-Zb1 were each tagged at the C terminals with His for purification. After being expressed in bacteria as in the method of Example 1, zHER2-Zb1 and scHER2-Zb1 were purified using Ni-NTA resin. igHER2-Zb1 was expression in animal cells and then purified using protein-A resin. The purified proteins were detected at predicted sizes (Zb1-His 7.3 kDa; zHER2-Zb1 14.4 kDa; scHER2-Zb1 49.5 kDa; igHER2-Zb1 heavy chain 57.5 kDa), as analyzed by SDS-PAGE (FIG. 3).

Example 2-2: Binding of Three HER2-Targeting Switch Molecules to Affibody Molecule (Antigen-Binding Site of Switchable CAR)

Three switch molecules (zHER2-Zb1, scHER2-Zb1, igHER2-Zb1) containing the affibody constructed in Example 2-1 were examined for binding an affibody (e.g., Zb2), which binds specifically to the affibody (Zb1) of the switch molecule. When three affibody (Zb1)-containing switch molecules (zHER2-Zb1, scHER2-Zb1, igHER2-Zb1) specifically bind to the coupled affibody molecule (Zb2), the affibodies which bind specifically to each other to form a pair can each be constructed into a switchable CAR system comprising an antigen-binding site of CAR and a switch molecule binding to the antigen-binding side of CAR.

Binding affinity of the affibody (Zb2) for the affibody (Zb1)-containing switch molecule was examined using a BLI assay. First, the switch molecules (zHER2-Zb1, scHER2-Zb1, and igHER2-Zb1) were each immobilized at a concentration of 200 nM for 15 min to AR2G sensor chip by an amine coupling approach using EDC/NHS as in Example 1. To the switch molecule protein-immobilized sensor, Zb2-Fc protein was coupled at a concentration of 200 nM for 15 min. Zb1-His was used as a positive control while bovine serum albumin (BSA) was used as a negative control. The results are depicted in FIG. 4.

Figure 4:
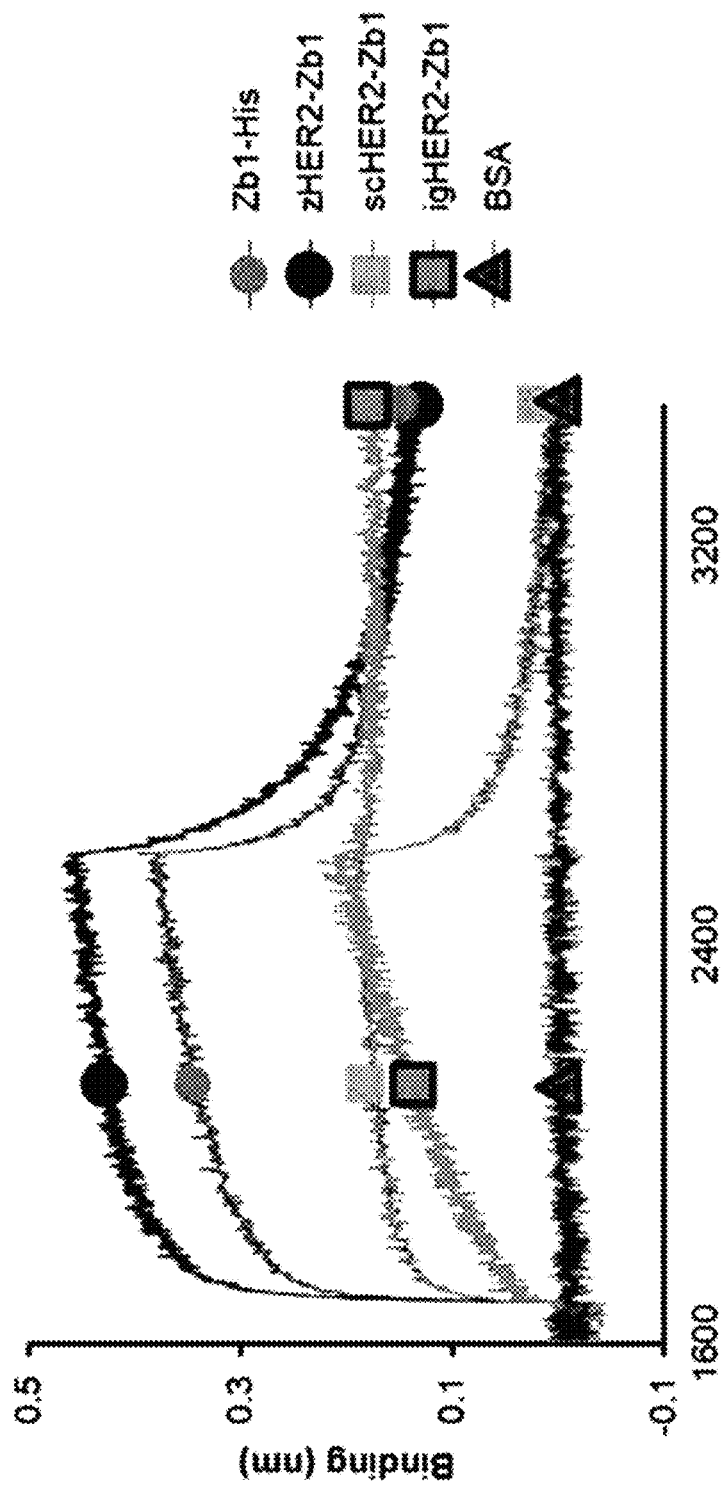
FIG. 4 is a view showing the direct binding of Zb2-Fc to a HER2-targeting switch molecule, as measured by BLI assay.

As shown in FIG. 4, Zb2-Fc was observed to bind specifically to all the three Zb1-containing switch molecules. From the results, it is understood that the affibodies which bind specifically to each other to form a pair can each be advantageously used in a switchable CAR system comprising the affibodies as an antigen binding site of CAR and a switch molecule binding to the antigen-binding site of CAR, respectively.

Figure 5A:
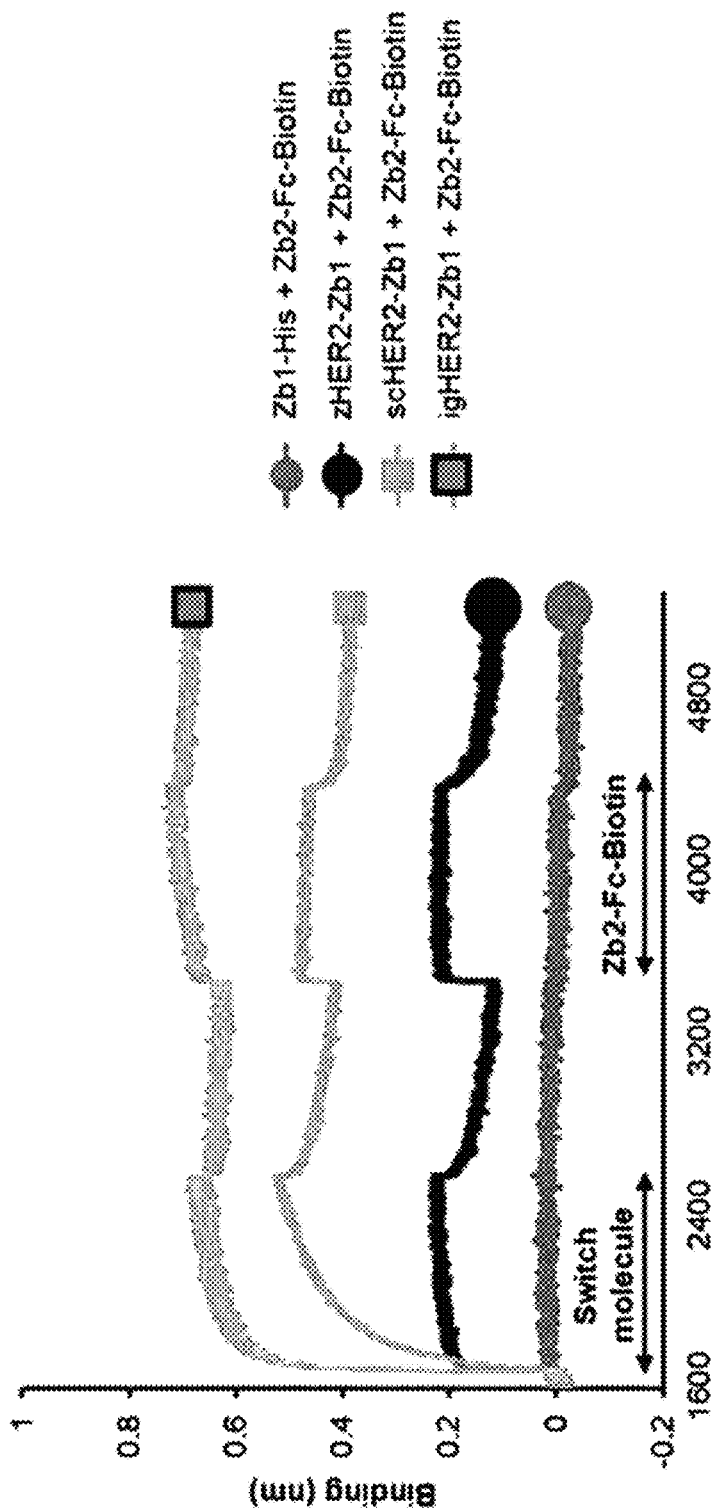
FIGS. 5A, 5B and 5C are views showing that HER2-targeting switch molecule and Zb2-Fc protein can be used for targeting HER2 protein and HER2-expressing cancer cells.

Example 2-3: Targeting Ability of Complex of Three HER2-Targeting Switch Molecules and Affibody Examination was made to see whether the affibodies which bind specifically to each other could be used as a switch molecule and a CAR recognizing the switch molecule. A complex in which each of the affibody-containing switch molecules of the present invention (e.g. zHER2-Zb1, scHER2-Zb1, and igHER2-Zb1) was coupled with a protein (e.g. Zb2-Fc) containing an affibody binding specifically to the affibody of the switch molecule was examined for ability to target a specific protein (e.g. HER2 protein), using a BLI assay. hHER2-ECD-His (human HER2 extracellular domain-His tag) was immobilized at a concentration of 10 mg/mL to AR2G sensor chip and coupled with 1 mM of the switch molecule for 15 min, followed by stabilizing the binding between the HER2 and the switch molecule. After the stabilization, Zb2-Fc-Biotin was applied at a concentration of 1 mg/mL for 15 min to the chip (FIG. 5a). The biotinylation of Zb2-Fc was achieved using EZ-Link sulfo-NHS-LC-Biotin (Thermo Fisher Scientific, Cat. No. 21335). The result indicates that the affibodies of the present invention, which form a pair (Zb pair), can be used as a switch molecule and an antigen-binding site of CAR, respectively and thus can target HER2 protein.

Figure 5B:
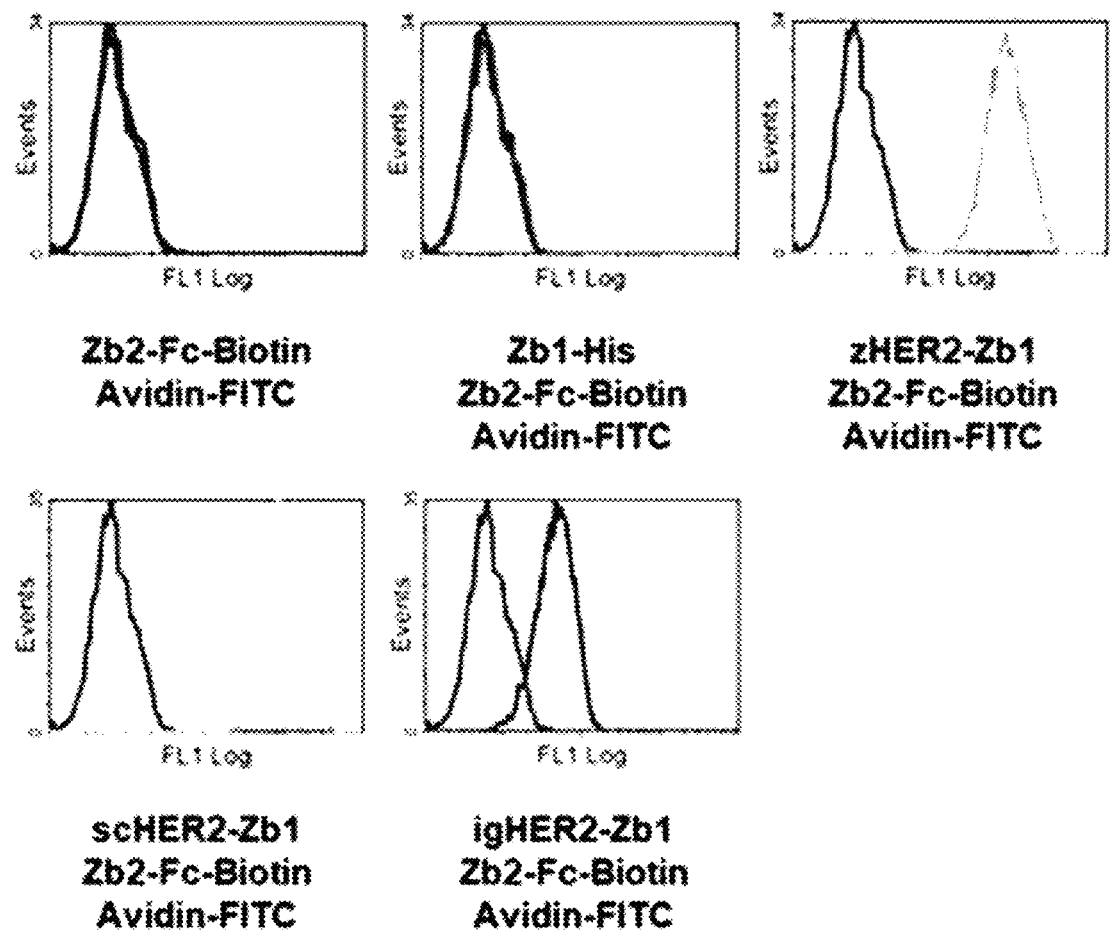
Figure 5C:
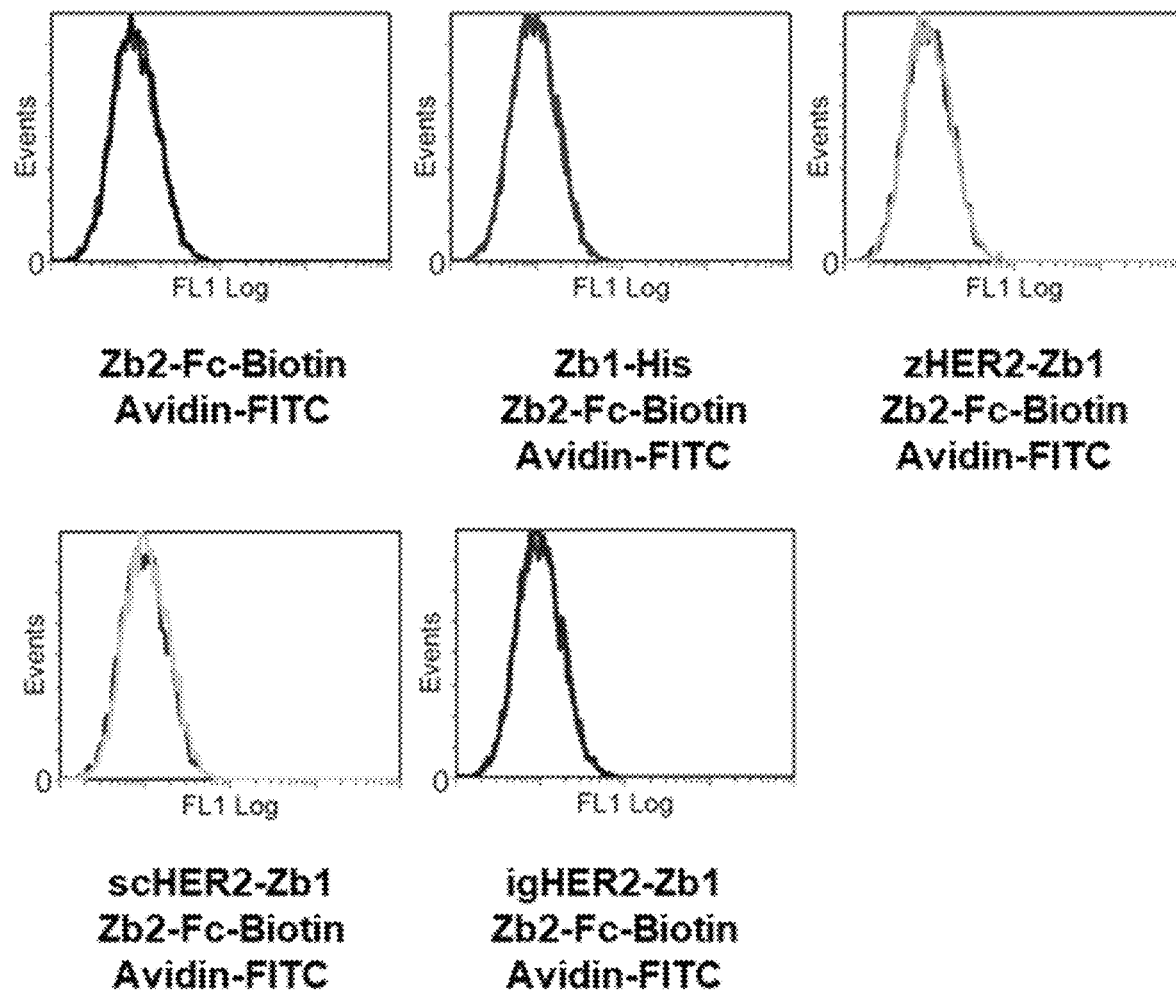

In addition, a flow cytometric assay was made to see whether a complex in which the switch molecule containing a HER2-targeting affibody (e.g. zHER2-Zb1, scHER2-Zb1, and igHER2-Zb1) and a protein (e.g. Zb2-Fc) containing an affibody specifically binding to the affibody are coupled with each other could selectively target HER2-positive cancer cells. OE-19 (ECACC, Cat. No. 96071721) was used as a HER2-positive cell while MDA-MB-231 (the Korean Cell Line Bank, Cat. No. 30026) was used as a HER2-negative cell. 1 mM of each of three purified switch molecules (zHER2-Zb1, scHER2-Zb1, and igHER2-Zb1) was applied to $5\times10^5$ cells of each of OE-19 and MDA-MB-231 and additionally treated with 1 mg/mL Zb2-Fc-Biotin to bind to each other. Avidin-FITC (Thermo Fisher Scientific, Cat. No. 29994), which can be coupled to Zb2-Fc-Biotin, was used for staining. Binding of the complex to cells was measured using Cytomics FC 500 (Beckman Coulter) (FIGS. 5b and 5c). As shown in FIGS. 5B and 5C, a combination of a switch molecule containing the affibody of the present invention and a corresponding affibody (Zb) protein was found to specifically target HER2-positive cancer cells.

Example 3: Construction of CD19-Targeting Switch Molecule by Using Affibody

Examination was made to see whether when used in combination with an antibody (antigen-binding fragment, scFv) capable of recognizing the B cell-derived carcinoma marker CD19, the affibody of the present invention could target CD19-positive cancer cells. Besides, with respect to the development of switch molecules, it was observed that binding properties were different depending on kinds of linkers via which a cancer marker-targeting region was linked to an affibody and targeting ability differed from one affibody to another. The CD19-targeting antibody disclosed in Korean Patent Application No. 10-2017-0178559 was fabricated in an scFv form and linked to the aforementioned affibody Zb1 (SEQ ID NOS: 1 and 2) or Zb2 ((SEQ ID NOS: 3 and 4) via linker $(G_4S)_3$ or $(S_4G)_3$ to construct switch molecule and then tagged at the C terminus with His for purification (FIG. 6).

TABLE 3

| SEQ ID NO: | Name | Type | Sequence (5'→3') |
|---|---|---|---|
| 17 | scCD19-(54G)3-Zb1 | Nucleotide | GAGGTGCAGCTGTTGGAGTCTGGGGGAGGCTT GGTACAGCCTGGGGGGTCCCTGAGACTCTCCT GTGCAGCCTCTGGATTCACCTTTAGCGATTATT ATATGAGCTGGGTCCGCCAGGCTCCAGGGAAG GGGCTGGAGTGGGTCTCAGGGATCTATTATGA TGGTTCGGCTAAGTATTACGCTGATTCTGTAAA AGGTCGGTTCACCATCTCCAGAGACAATTCCAA GAACACGCTGTATCTGCAAATGAACAGCCTGA GAGCCGAGGACACGGCCGTGTATTACTGTGCG AAAGGTCCTAATTTTTGTAATGATCGGACTTGTT CTTATTATTATGCTATGGACGTCTGGGGCCAGG GTACACTGGTCACCGTGAGCTCAGGTGGAGGC GGTTCAGGCGGAGGTGGATCCGGCGGTGGCG GATCGCAGTCTGTGCTGACTCAGCCACCCTCA GCGTCTGGGACCCCCGGGCAGAGGGTCACCA TCTCTTGTTATGGTCAGCCGTCTAATATTGGCA GTAATGCTGTCTACTGGTACCAGCAGCTACCAG GAACGGCCCCCAAACTCCTCATCTATGATGATA ATCATCGGCCAAGCGGGGTCCCTGACCGATTC |

TABLE 3-continued

| SEQ ID NO: | Name | Type | Sequence (5'→3') |
|---|---|---|---|
| | | | TCTGGCTCCAAGTCTGGCACCTCAGCCTCCCT GGCCATCAGTGGGCTCCGGTCCGAGGATGAG GCTGATTATTACTGTGGTACCTGGGATTATAGC CTGAGTGGTTATGTCTTAGGCGGAGGCACCAA GCTGACGGTCCTATCATCAAGCAGTGGAAGTT CTTCATCCGGCTCATCATCTTCAGGTGTCGATA ACAAATTCAACAAAGAGCTGGGCTGGGCTACC TGGGAGATTTTTAATCTTCCGAATTTAAACGGT GTTCAAGTGAAAGCTTTTATCGATAGCCTGCGC GACGATCCTAGCCAGAGCGCAAATTTGCTGGC CGAAGCAAAAAAACTGAATGATGCGCAGGCGC CAAAG |
| 18 | | Amino acid | EVQLLESGGGLVQPGGSLRLSCAASGFTFSDYY MSWVRQAPGKGLEVVVSGIYYDGSAKYYADSVK GRFTISRDNSKNTLYLQMNSLRAEDTAVYYCAKG PNFCNDRTCSYYYAMDVWGQGTLVTVSSGGGG SGGGGSGGGGSQSVLTQPPSASGTPGQRVTISC YGQPSNIGSNAVYWYQQLPGTAPKLLIYDDNHRP SGVPDRFSGSKSGTSASLAISGLRSEDEADYYCG TWDYSLSGYVLGGGTKLTVLSSSSGSSSSGSSS SGVDNKFNKELGWATWEIFNLPNLNGVQVKAFID SLRDDPSQSANLLAEAKKLNDAQAPK |
| 19 | scCD19-(G4S)3-Zb1 | Nucleotide | GAGGTGCAGCTGTTGGAGTCTGGGGGAGGCTT GGTACAGCCTGGGGGGTCCCTGAGACTCTCCT GTGCAGCCTCTGGATTCACCTTTAGCGATTATT ATATGAGCTGGGTCCGCCAGGCTCCAGGGAAG GGGCTGGAGTGGGTCTCAGGGATCTATTATGA TGGTTCGGCTAAGTATTACGCTGATTCTGTAAA AGGTCGGTTCACCATCTCCAGAGACAATTCCAA GAACACGCTGTATCTGCAAATGAACAGCCTGA GAGCCGAGGACACGGCCGTGTATTACTGTGCG AAAGGTCCTAATTTTTGTAATGATCGGACTTGTT CTTATTATTATGCTATGGACGTCTGGGGCCAGG GTACACTGGTCACCGTGAGCTCAGGTGGAGGC GGTTCAGGCGGAGGTGGATCCGGCGGTGGCG GATCGCAGTCTGTGCTGACTCAGCCACCCTCA GCGTCTGGGACCCCCGGGCAGAGGGTCACCA TCTCTTGTTATGGTCAGCCGTCTAATATTGGCA GTAATGCTGTCTACTGGTACCAGCAGCTACCAG GAACGGCCCCCAAACTCCTCATCTATGATGATA ATCATCGGCCAAGCGGGGTCCCTGACCGATTC TCTGGCTCCAAGTCTGGCACCTCAGCCTCCCT GGCCATCAGTGGGCTCCGGTCCGAGGATGAG GCTGATTATTACTGTGGTACCTGGGATTATAGC CTGAGTGGTTATGTCTTAGGCGGAGGCACCAA GCTGACGGTCCTAGGTGGAGGTGGTAGTGGTG GTGGTGGTAGTGGTGGTGGAGGTAGTGTCGAT AACAAATTCAACAAAGAGCTGGGCTGGGCTAC CTGGGAGATTTTTAATCTTCCGAATTTAAACGG TGTTCAAGTGAAAGCTTTTATCGATAGCCTGCG CGACGATCCTAGCCAGAGCGCAAATTTGCTGG CCGAAGCAAAAAAACTGAATGATGCGCAGGCG CCAAAG |
| 20 | | Amino acid | EVQLLESGGGLVQPGGSLRLSCAASGFTFSDYY MSWVRQAPGKGLEVVVSGIYYDGSAKYYADSVK GRFTISRDNSKNTLYLQMNSLRAEDTAVYYCAKG PNFCNDRTCSYYYAMDVWGQGTLVTVSSGGGGS GGGGSGGGGSQSVLTQPPSASGTPGQRVTISCY GQPSNIGSNAVYWYQQLPGTAPKLLIYDDNHRP SGVPDRFSGSKSGTSASLAISGLRSEDEADYYC GTWDYSLSGYVLGGGTKLTVLGGGGSGGGGSGG GGSVDNKFNKELGWATWEIFNLPNLNGVQVKAF IDSLRDDPSQSANLLAEAKKLNDAQAPK |
| 21 | scCD19-(S4G)3-Zb2 | Nucleotide | GAGGTGCAGCTGTTGGAGTCTGGGGGAGGCTT GGTACAGCCTGGGGGGTCCCTGAGACTCTCCT GTGCAGCCTCTGGATTCACCTTTAGCGATTATT ATATGAGCTGGGTCCGCCAGGCTCCAGGGAAG GGGCTGGAGTGGGTCTCAGGGATCTATTATGA TGGTTCGGCTAAGTATTACGCTGATTCTGTAAA AGGTCGGTTCACCATCTCCAGAGACAATTCCAA GAACACGCTGTATCTGCAAATGAACAGCCTGA GAGCCGAGGACACGGCCGTGTATTACTGTGCG AAAGGTCCTAATTTTTGTAATGATCGGACTTGTT CTTATTATTATGCTATGGACGTCTGGGGCCAGG GTACACTGGTCACCGTGAGCTCAGGTGGAGGC |

TABLE 3-continued

| SEQ ID NO: | Name | Type | Sequence (5'→3') |
|---|---|---|---|
| | | | GGTTCAGGCGGAGGTGGATCCGGCGGTGGCG GATCGCAGTCTGTGCTGACTCAGCCACCCTCA GCGTCTGGGACCCCCGGGCAGAGGGTCACCA TCTCTTGTTATGGTCAGCCGTCTAATATTGGCA GTAATGCTGTCTACTGGTACCAGCAGCTACCAG GAACGGCCCCCAAACTCCTCATCTATGATGATA ATCATCGGCCAAGCGGGGTCCCTGACCGATTC TCTGGCTCCAAGTCTGGCACCTCAGCCTCCCT GGCCATCAGTGGGCTCCGGTCCGAGGATGAG GCTGATTATTACTGTGGTACCTGGGATTATAGC CTGAGTGGTTATGTCTTAGGCGGAGGCACCAA GCTGACGGTCCTATCATCAAGCAGTGGAAGTT CTTCATCCGGCTCATCATCTTCAGGTGTCGATA ACAAATTCAACAAAGAGCGCGTAATTGCAATCG GTGAAATTATGCGTCTGCCAAACCTGAATAGCC TGCAGGTTGTGGCCTTTATAAACTCTCTGCGCG ATGACCCGAGTCAGTCAGCAAACCTGCTTGCG GAAGCGAAAAAGCTGAATGATGCCCAAGCTCC TAAA |
| 22 | | Amino acid | EVQLLESGGGLVQPGGSLRLSCAASGFTFSDYY MSWVRQAPGKGLEVVVSGIYYDGSAKYYADSVK GRFTISRDNSKNTLYLQMNSLRAEDTAVYYCAKG PNFCNDRTCSYYYAMDVWGQGTLVTVSSGGGG SGGGGSGGGGSQSVLTQPPSASGTPGQRVTISC YGQPSNIGSNAVYWYQQLPGTAPKLLIYDDNHRP SGVPDRFSGSKSGTSASLAISGLRSEDEADYYCG TWDYSLSGYVLGGGTKLTVLSSSSGSSSSGSSS SGVDNKFNKERVIAIGEIMRLPNLNSLQVVAFI NSLRDDPSQSANLLAEAKKLNDAQAPK |
| 23 | scCD19-(G4S)3-Zb2 | Nucleotide | GAGGTGCAGCTGTTGGAGTCTGGGGGAGGCTT GGTACAGCCTGGGGGGTCCCTGAGACTCTCCT GTGCAGCCTCTGGATTCACCTTTAGCGATTATT ATATGAGCTGGGTCCGCCAGGCTCCAGGGAAG GGGCTGGAGTGGGTCTCAGGGATCTATTATGA TGGTTCGGCTAAGTATTACGCTGATTCTGTAAA AGGTCGGTTCACCATCTCCAGAGACAATTCCAA GAACACGCTGTATCTGCAAATGAACAGCCTGA GAGCCGAGGACACGGCCGTGTATTACTGTGCG AAAGGTCCTAATTTTTGTAATGATCGGACTTGTT CTTATTATTATGCTATGGACGTCTGGGGCCAGG GTACACTGGTCACCGTGAGCTCAGGTGGAGGC GGTTCAGGCGGAGGTGGATCCGGCGGTGGCG GATCGCAGTCTGTGCTGACTCAGCCACCCTCA GCGTCTGGGACCCCCGGGCAGAGGGTCACCA TCTCTTGTTATGGTCAGCCGTCTAATATTGGCA GTAATGCTGTCTACTGGTACCAGCAGCTACCAG GAACGGCCCCCAAACTCCTCATCTATGATGATA ATCATCGGCCAAGCGGGGTCCCTGACCGATTC TCTGGCTCCAAGTCTGGCACCTCAGCCTCCCT GGCCATCAGTGGGCTCCGGTCCGAGGATGAG GCTGATTATTACTGTGGTACCTGGGATTATAGC CTGAGTGGTTATGTCTTAGGCGGAGGCACCAA GCTGACGGTCCTAGGTGGAGGTGGTAGTGGTG GTGGTGGTAGTGGTGGTGGAGGTAGTGTCGAT AACAAATTCAACAAAGAGCGCGTAATTGCAATC GGTGAAATTATGCGTCTGCCAAACCTGAATAGC CTGCAGGTTGTGGCCTTTATAAACTCTCTGCGC GATGACCCGAGTCAGTCAGCAAACCTGCTTGC GGAAGCGAAAAAGCTGAATGATGCCCAAGCTC CTAAA |
| 24 | | Amino acid | EVQLLESGGGLVQPGGSLRLSCAASGFTFSDYY MSWVRQAPGKGLEVVVSGIYYDGSAKYYADSVK GRFTISRDNSKNTLYLQMNSLRAEDTAVYYCAK GPNFCNDRTCSYYYAMDVWGQGTLVTVSSGGGG SGGGGSGGGGSQSVLTQPPSASGTPGQRVTISC YGQPSNIGSNAVYWYQQLPGTAPKLLIYDDNHRP SGVPDRFSGSKSGTSASLAISGLRSEDEADYYCG TWDYSLSGYVLGGGTKLTVLGGGGSGGGGSGG GGSVDNKFNKERVIAIGEIMRLPNLNSLQVVAF INSLRDDPSQSANLLAEAKKLNDAQAPK |

Figure 7A:
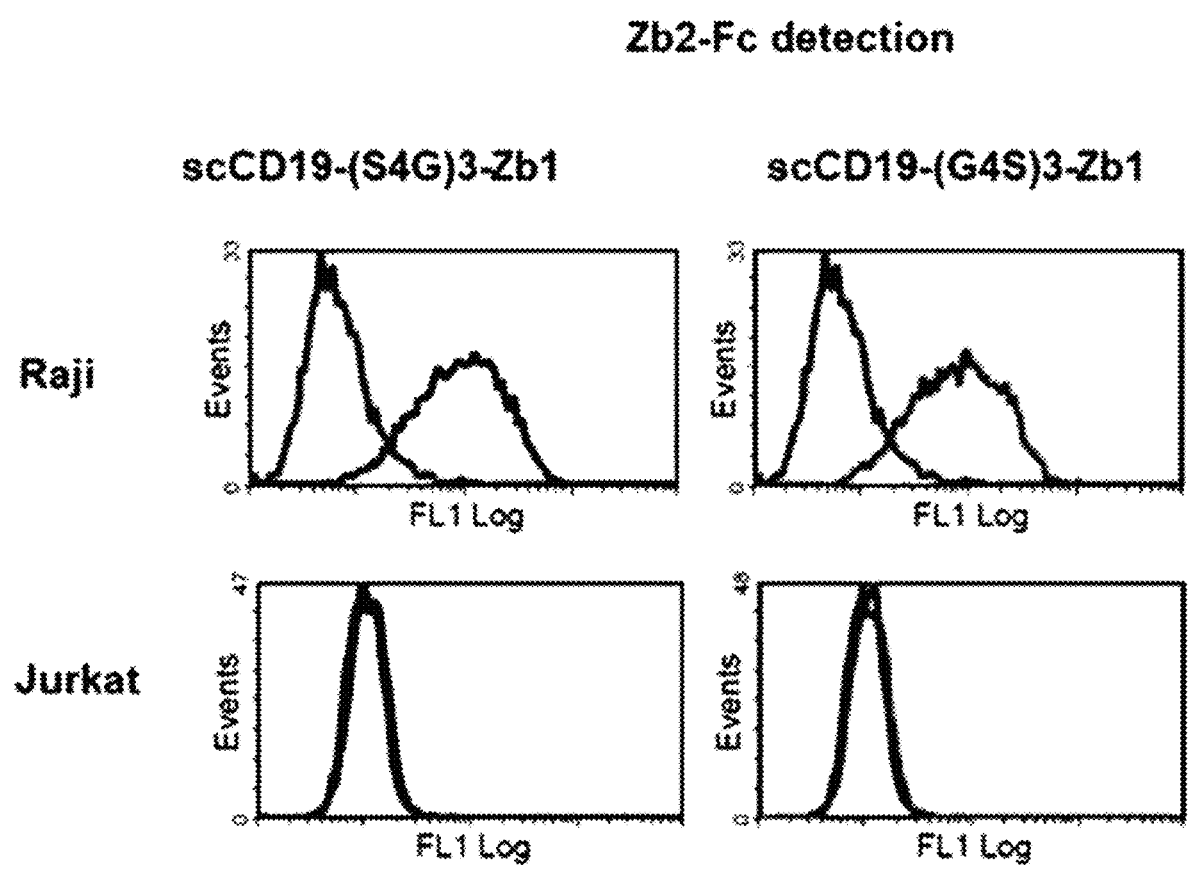
FIGS. 7A and 7B are views showing that CD19-targeting switch molecule and affibody can be used for selectively targeting CD19-positive cancer cells.
Figure 7B:
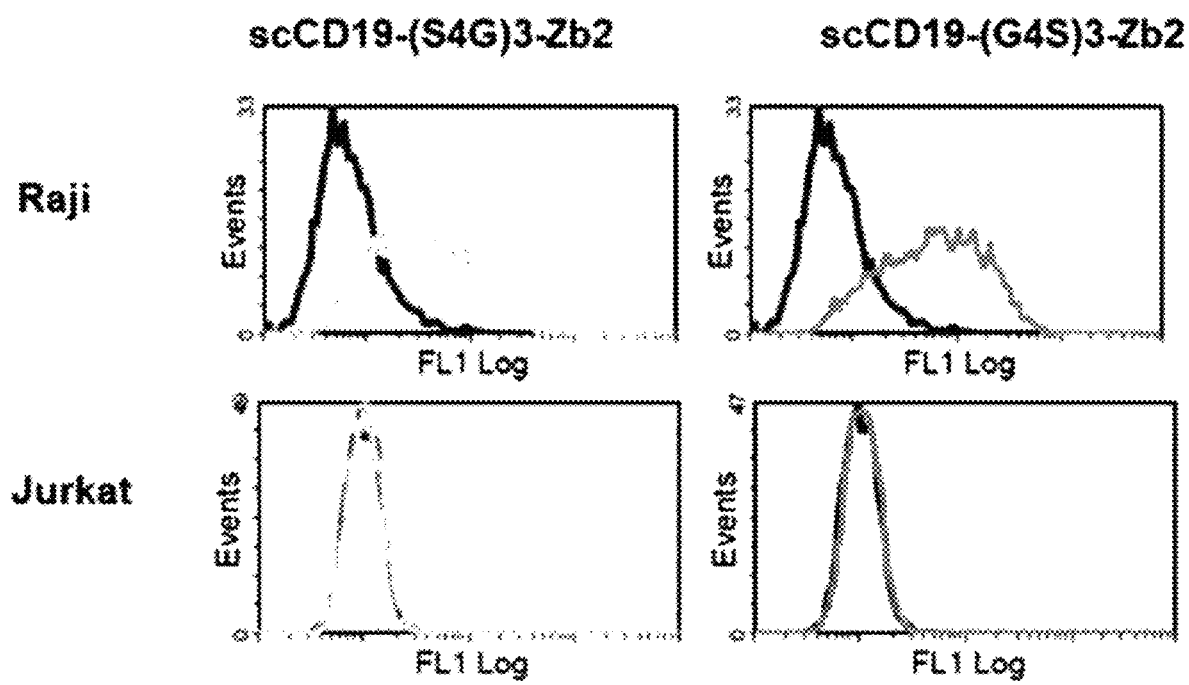

The switch molecules were expressed in bacteria as in Example 1 and purified using Ni-NTA resin. To examine the ability of the switch molecules to target CD19-expressing cancer cells, CD19-positive Raji cells (ATCC, CCL-86) and CD19-negative Jurkat cells (ATCC, TIB-152) were treated with the constructed switch molecule and the affibody protein and analyzed by flow cytometry. CD19-positive cancer Raji cells and CD19-negative Jurkat cells were incubated with 2 mg of each of the switch molecules [scCD19-$(S_4G)_3$-Zb1, scCD19-$(G_4S)_3$-Zb1, scCD19-$(S_4G)_3$-Zb2, and scCD19-$(G_4S)_3$-Zb2] and then with Zb1-Fc or Zb2-Fc, followed by detection with anti-hIgG-FITC (Invitrogen, Cat. No. A11013) (FIGS. 7a and 7b). As can be seen in FIGS. 7a and 7b, the switch molecules comprising the CD19-targeting scFv and the affibody (Zb1 or Zb2) were found to target CD19-positive Raji cells, but not CD19-negative Jurkat cells. Therefore, the CD19-targeting switch molecule comprising the affibody according to the present invention was found to specifically target CD19.

From the result, it is understood that the switch molecule of the present invention, comprising (a) a targeting moiety binding to a target antibody such as an antibody, an antigen-binding fragment, or an affibody and (b) an affibody as a polypeptide binding to CAR, can bind specifically to various target antigens as various kinds of targeting moieties are employed. In addition, the switch molecule of the present invention allows any combination of affibodies and linkers irrespective of kinds of the affibody (e.g. Zb1, Zb2) as the polypeptide binding to CAR and kinds of the linker [$(S4G)3$, $(G4S)3$].

Example 4: Construction of Lentivirus Containing Affibody-Liked Chimeric Antigen Receptor Chimeric antigen receptor T (CAR-T) cells developed with a combination of Zb1 and Zb2 affibodies and CAR-T cells developed with the switch molecule were assayed for cytokine secretion activity and cytotoxicity against target cells. In this regard, a chimeric antigen receptor comprising Zb2 was developed. The chimeric antigen receptor was composed of a CD8 leader, Zb2, a CD8 hinge, a transmembrane domain, a CD137 cytoplasmic domain, and a cytoplasmic domain of CD3 zeta. After being subjected to codon optimization for a chimeric antigen receptor, the gene was cut with SpeI/PacI and ligated to pLenti6.3/V5-TOPO lentiviral vector (Invitrogen, K5315-20) in which the promotor had been modified into EF-1 alpha. The constructs thus obtained were identified by base sequencing.

TABLE 4

| SEQ ID NO: | Name | Type | Sequence (5'→3') |
|---|---|---|---|
| 25 | Codon-optimized Zb2 | Nucleotide | GTCGATAACAAATTCAATAAGGAACGCGTGATTG CCATTGGCGAGATCATGCGCCTGCCCAATCTGAA TAGCTTGCAGGTGGTGGCCTTTATCAACTCCCTT CGGGATGACCCATCACAGTCTGCCAACCTCCTGG CTGAGGCAAAGAAGCTCAACGACGCGCAGGCTC CTAAA |
| 26 | | Amino acid | VDNKFNKERVIAIGEIMRLPNLNSLQVVAFINSL RDDPSQSANLLAEAKKLNDAQAPK |
| 27 | CAR construct (CD8 hinge-TM-CD137-CD3z) | Nucleotide | ACCACAACTCCAGCTCCCCGGCCCCCTACCCCTG CACCAACAATCGCCAGCCAGCCTCTGTCCCTGAG ACCAGAGGCATGTAGGCCAGCTGCAGGAGGAGC AGTGCATACAAGAGGCCTGGACTTCGCCTGCGAT ATCTACATTTGGGCTCCTCTGGCAGGAACTTGTG GCGTGCTGCTGCTGTCTCTGGTCATCACCCTGTA CTGCAAAAGGGGCCGCAAGAAACTGCTGTATATT TTCAAGCAGCCCTTCATGCGGCCCGTGCAGACCA CACAGGAGGAAGACGGGTGCTCCTGTAGATTCC CCGAGGAAGAGGAAGGCGGGTGTGAGCTGCGC GTCAAGTTCAGCCGATCAGCCGATGCTCCTGCAT ACAAGCAGGGCCAGAATCAGCTGTATAACGAGCT GAATCTGGGGCGCCGAGAGGAATACGACGTGCT GGATAAGCGGAGAGGGAGGGACCCCGAAATGGG AGGCAAACCTAGGCGCAAGAACCCACAGGAGGG ACTGTACAATGAACTGCAGAAGGACAAAATGGCC GAGGCTTATTCCGAAATTGGGATGAAAGGAGAGC GACGGAGAGGGAAGGGACACGATGGGCTGTATC AGGGACTGTCTACCGCCACTAAAGATACCTACGA CGCTCTGCACATGCAGGCTCTGCCACCTCGCTGA |
| 28 | | Amino acid | TTTPAPRPPTPAPTIASQPLSLRPEACRPAAGGA VHTRGLDFACDIYIWAPLAGTCGVLLLSLVITLY CKRGRKKLLYIFKQPFMRPVQTTQEEDGCSCRFP EEEEGGCELRVKFSRSADAPAYKQGQNQLYNELN LGRREEYDVLDKRRGRDPEMGGKPRRKNPQEGLY NELQKDKMAEAYSEIGMKGERRRGKGHDGLYQGL STATKDTYDALHMQALPPR |
| 29 | CD8 leader | Amino acid | MALPVTALLLPLALLLHAARP |

Each of the prepared lentiviral constructs was transduced, together with the plasmid pCMV-dR8.91 carrying viral coat protein VSV-G (vesicular stomatitis Indiana virus G protein), gag, pol, and rev genes, into Lenti-X 293T cells (Takara Bio Inc., Japan). Transduction was performed using Lipofectamine 2000 (Invitrogen, USA) according to the manufacturer's protocol. The cell culture containing lentivirus was enriched with Lenti-X concentrator (Takara Bio Inc., Japan) and stored at −80° C.

Example 5: Preparation and Activity of T Cell Displaying Developed Affibody-Bearing Chimeric Antigen Receptor on Surface Cytotoxic T cells on which Zb2-bearing chimeric antigen receptors were displayed were prepared using the lentivirus obtained in Example 4. First, cells were isolated from human blood and stimulated with Dynabeads™ Human T-Activator CD3/CD28 (Thermofisher scientific, 11131D). Thereafter, the lentivirus was transduced for 24 hours into the cells in the presence of polybrene (Sigma-Aldrich, H9268). Then, the medium was exchanged with a medium containing IL-2 (Gibco, CTP0021), followed by incubation at 37° C. in a 5% $CO_2$ atmosphere. T cells presenting the Zb2-bearing chimeric antigen receptor on the surface thereof (Zb2.CART cells) were used to analyze the Zb1-bearing switch molecule for cancer cell clearance and cytokine secretion activity.

The HER2-positive cell line SK-OV3 was employed in the experiment. First, SK-OV3 cells were seeded at a density of $3 \times 10^4$ cells per well into round-bottom 96-well plates. The prepared cytotoxic T cells were added to the SK-OV3-seeded plates at a rate of 1:5 of SK-OV3: cytotoxic T cells per well. zHER2-Zb1 was added at predetermined concentrations to individual wells and incubated at 37° C. for 24 hours in a 5% $CO_2$ atmosphere. Thereafter, interferon gamma secreted to the medium was quantitated using Human IFN-γ ELISA set (BD Bioscience, 555142) according to the manufacturer's protocol. Cytotoxicity of the cytotoxic T cells was analyzed using a luminescence assay (CytoTox-Glo Cytotoxicity Assay, Promega, G9292).

Figure 8A:
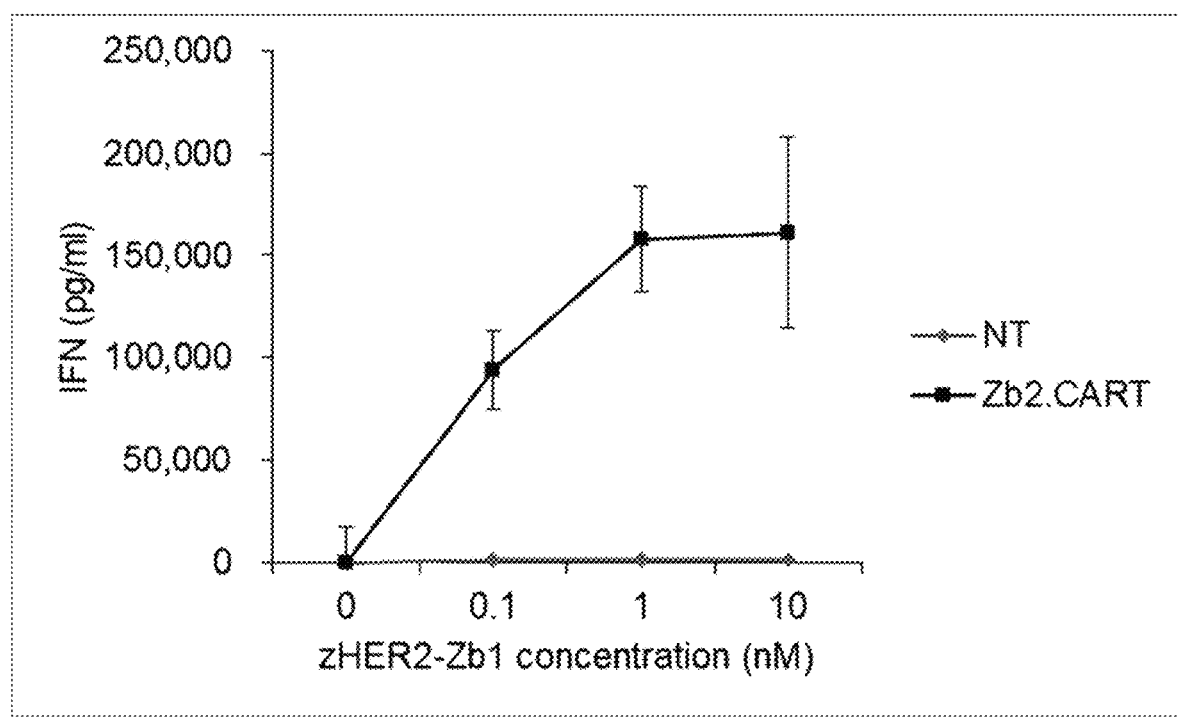
FIGS. 8A and 8B are views showing HER2-specific CAR-T cell activity against HER2-positive SK-OV3 cells by using T cells expressing a Zb2 affibody-bearing chimeric antigen receptor (Zb2.CART) and a HER2-targeting switch molecule comprising Zb1(zHER2-Zb1). SK-OV3 cells and Zb2.CART cells were co-cultured at a rate of 1:5 with the switch molecule (zHER2-Zb1) for 24 hours.

As can be seen in FIG. 8a, the experimental group treated with the cytotoxic T cells containing the antibody fragment of the present invention and SK-OV3 was observed to significantly increase in the secretion of interferon gamma depending on the amount of zHER2-Zb1 used.

Figure 8B:
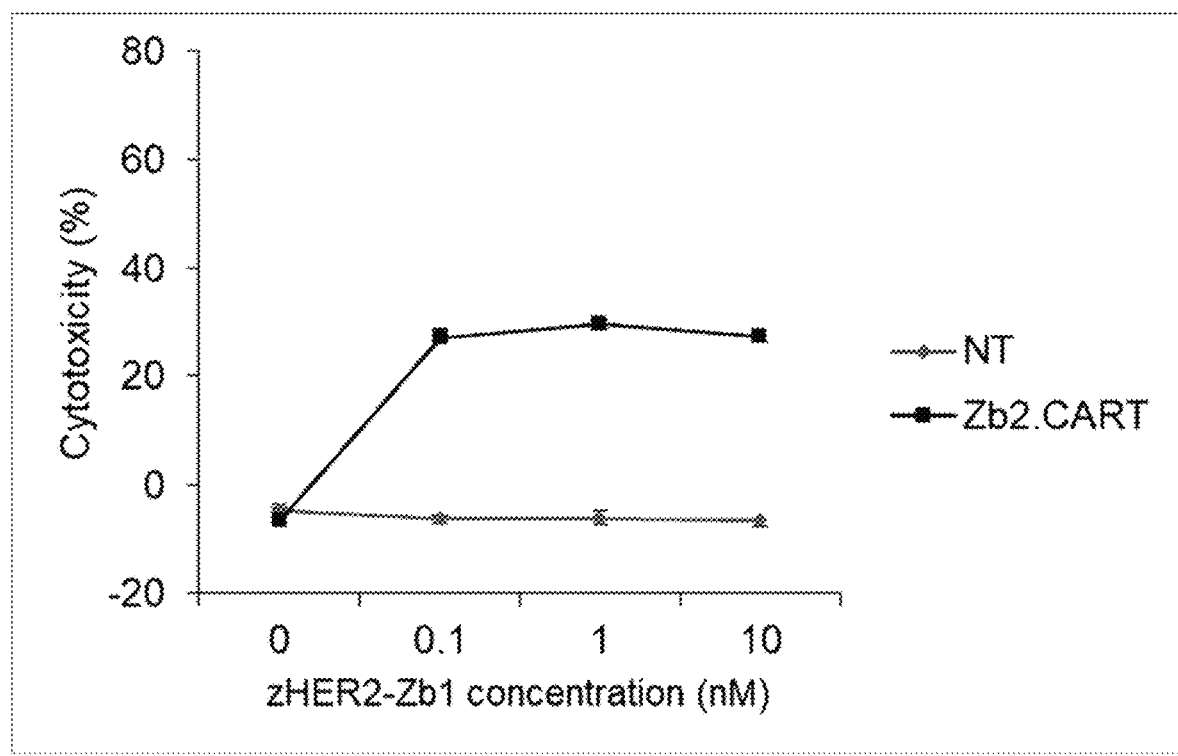

Cytotoxic effects of the chimeric antigen receptor comprising the affibody Zb2 of the present invention were measured using CytoTox-Glo Cytotoxicity Assay after co-culturing cytotoxic T cells, SK-OV3, and zHER2-Zb1. Relative lysis rates were given when the signal from the wells where only SK-OV3 cells had been cultured was set forth as 100%. The Zb2-bearing chimeric antigen receptor T cells exhibited a cytotoxic effect in the experimental group treated with zHER2-Zb1 (FIG. 8b). Neither cytokine secretion nor cytotoxicity was detected in the absence of the switch molecule (zHER2-Zb1). Thus, the cytokine secretion and cytotoxicity of the CAR-T cells tested was attributed to the ability of a combination of affibodies Zb1 and Zb2 to target cancer cells.

This application contains references to amino acid sequences and/or nucleic acid sequences which have been submitted herewith as the sequence listing text file. The aforementioned sequence listing is hereby incorporated by reference in its entirety pursuant to 37 C.F.R. § 1.52(e).

What is claimed is:

1. A switch molecule for activating a chimeric antigen receptor-effector cell, the molecule comprising:
   a targeting moiety binding to a cell surface molecule on a target cell; and
   an affibody specifically binding to an extracellular domain of the chimeric antigen receptor (CAR) on the effector cell, wherein
   the switch molecule comprises an amino acid sequence selected from the group consisting of:
   i) the amino acid sequence of SEQ ID NO: 10;
   ii) the amino acid sequence of SEQ ID NO: 10, wherein amino acids 74 to 131 of SEQ ID NO: 10 are replaced with amino acids 1 to 58 of SEQ ID NO: 4;
   iii) the amino acid sequence of SEQ ID NO: 12;
   iv) the amino acid sequence of SEQ ID NO: 12, wherein amino acids 259 to 316 are replaced with amino acids 1 to 58 of SEQ ID NO: 4;
   v) the amino acid sequence of SEQ ID NO: 14;
   vi) the amino acid sequence of SEQ ID NO: 14, wherein amino acids 466 to 523 are replaced with amino acids 1 to 58 of SEQ ID NO: 4;
   vii) the amino acid sequence of SEQ ID NO: 18;
   viii) the amino acid sequence of SEQ ID NO: 20;
   ix) the amino acid sequence of SEQ ID NO: 22; and
   x) the amino acid sequence of SEQ ID NO: 24.

2. The switch molecule of claim 1, wherein activation of the effector cell results in cytotoxicity against a target cell, cytokine secretion, or a combination thereof.

* * * * *